US010132942B2

(12) United States Patent
Frisch et al.

(10) Patent No.: US 10,132,942 B2
(45) Date of Patent: Nov. 20, 2018

(54) POSITRON-EMISSION TOMOGRAPHY DETECTOR SYSTEMS BASED ON LOW-DENSITY LIQUID SCINTILLATORS AND PRECISE TIME-RESOLVING PHOTODETECTORS

(71) Applicants: The University of Chicago, Chicago, IL (US); Brookhaven Science Associates, LLC, Upton, NY (US)

(72) Inventors: Henry J. Frisch, Chicago, IL (US); Eric J. Oberla, Chicago, IL (US); Hee-Jong Kim, Naperville, IL (US); Minfang Yeh, Stony Brook, NY (US)

(73) Assignees: The University of Chicago, Chicago, IL (US); Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 15/553,275

(22) PCT Filed: Apr. 8, 2016

(86) PCT No.: PCT/US2016/026640
§ 371 (c)(1),
(2) Date: Aug. 24, 2017

(87) PCT Pub. No.: WO2016/168076
PCT Pub. Date: Oct. 20, 2016

(65) Prior Publication Data

US 2018/0038968 A1 Feb. 8, 2018

Related U.S. Application Data

(60) Provisional application No. 62/163,538, filed on May 19, 2015, provisional application No. 62/146,780, filed on Apr. 13, 2015.

(51) Int. Cl.
*G01T 1/29* (2006.01)
*G01T 1/20* (2006.01)
(Continued)

(52) U.S. Cl.
CPC ............ *G01T 1/2985* (2013.01); *G01T 1/204* (2013.01); *A61B 6/037* (2013.01); *G01T 1/2018* (2013.01)

(58) Field of Classification Search
CPC ....... A61B 6/037; G01T 1/2018; G01T 1/204; G01T 1/2985
See application file for complete search history.

(56) References Cited

U.S. PATENT DOCUMENTS 5,793,045 A * 8/1998 DiFilippo ............. G01T 1/2985 250/363.03
7,414,246 B2 8/2008 Griesmer et al.
(Continued)

OTHER PUBLICATIONS

Yeh, Minfang, "Water-based Liquid Scintillator." NNN-2014, Nov. 6, 2014 (Nov. 6, 2014), p. 2, 5 [online] URL=<http://indico.in2p3.fr/event/10050/session/4/contribution/20/material/slides/0.pdf>.*
(Continued)

*Primary Examiner* — Mark R Gaworecki
(74) *Attorney, Agent, or Firm* — Bell & Manning, LLC

(57) ABSTRACT

TOF-PET detector systems, and methods for imaging photon-emitting samples using the detector systems, are provided. The TOF-PET detector systems use large-area photodetectors with extremely high time-resolution and an approach to data collection and analysis that allows for the use of inexpensive low-density scintillator materials. The TOF-PET detector systems are characterized by their ability to identify, on a statistical basis, the transverse and depth location of the first of the series of energy deposition events that are generated when a gamma photon enters the low-density scintillator material.

27 Claims, 21 Drawing Sheets

(51) Int. Cl.

| | |
|---|---|
| ***G01T 1/204*** | (2006.01) |
| *A61B 6/03* | (2006.01) |

(56) References Cited

U.S. PATENT DOCUMENTS

| | | | | |
|---|---|---|---|---|
| 8,476,593 | B2 * | 7/2013 | Degenhardt ............ | G01T 1/249<br>250/362 |
| 2010/0108896 | A1 | 5/2010 | Surti et al. | |
| 2011/0001049 | A1 | 1/2011 | Shibuya et al. | |
| 2011/0284757 | A1 * | 11/2011 | Butuceanu ........... | A61N 5/1048<br>250/389 |
| 2014/0110592 | A1 | 4/2014 | Nelson et al. | |

OTHER PUBLICATIONS

International Search Report and Written Opinion mailed in PCT Patent Application No. PCT/US16/26640, dated Jul. 12, 2016.

M. Conti, Focus on time-of-flight PET: the benefits of improved time resolution, Eur J Nucl Med Mol Imaging 38, Jan. 13, 2011, pp. 1147-1157.

G.B. Saha, Data Acquisition and Corrections, Basics of PET Imaging: Physics, Chemistry, and Regulations, 2010, pp. 41-69.

R. E. Schmitz, A. M. Alessio and P. E. Kinahan, 2005. The physics of PET/CT scanners in "PET and PET/CT: A clinical guide", 2nd Ed, E. Lin and A. Alavi, Thieme Ch 1.

Moskal et al., TOF-PET Detector Concept Based on Organic Scintillators, Nuclear Medicine Review 2012, 15, Suppl. C: C81-C84; arXiv:1305.5559.

Moses et al., Scintillators for Positron Emission Tomography, Presented at SCINT '95, Delft, The Netherlands, 1995.

H. Frisch, The Development of Large-Area Thin Planar Psec Photodetectors, Presentation at Enrico Fermi Institute Colloquium, May 2, 2011.

Kim et al., A Design of a PET Detector Using Micro-Channel Plate Photomultipliers with Transmission-Line Readout, Nucl Instrum Methods Phys Res A. 622(3), 2010.

* cited by examiner

POSITRON-EMISSION TOMOGRAPHY DETECTOR SYSTEMS BASED ON LOW-DENSITY LIQUID SCINTILLATORS AND PRECISE TIME-RESOLVING PHOTODETECTORS

CROSS-REFERENCE TO RELATED APPLICATIONS

The present application is a National Stage Entry of International Application No. PCT/US2016/026640 that was filed Apr. 8, 2016; the entire contents of which are hereby incorporated by reference, which claims priority to U.S. Provisional Patent Application No. 62/146,780 that was filed Apr. 13, 2015 and U.S. Provisional Patent Application No. 62/163,538 that was filed May 19, 2015; the entire contents of which are hereby incorporated by reference.

REFERENCE TO GOVERNMENT RIGHTS

This invention was made with government support under DOE award De-SC0008172, DE-AC02-98CH10886, DE-SC0012704, and NSF grant PHY-1066014. The government has certain rights in the invention.

BACKGROUND

Positron-emission tomography (PET) has unique capabilities in diagnostics as it is sensitive to enhanced biological activity caused by trauma or disease. For example, it is highly effective in locating hairline bone fractures that can be difficult to identify by X-rays. However PET has operational drawbacks that preclude its widespread use for a broad range of diagnostics: it involves a large dose of radioactive tracer to the patient; it has limited resolution due to gamma ray scattering and statistics; PET cameras use expensive scintillator crystals; and it requires an extensive supporting infrastructure. As a result, PET is currently limited in use to large facilities, largely in cities in highly developed countries.

Current PET camera designs require expensive high-density scintillator crystals to provide good spatial resolution when viewed solely from the back face of the crystal array. The depth of interaction of the gamma rays in the scintillator is not measured directly, and a high density ameliorates the blurring of the interaction point due to the concomitant uncertainty. However the uncertainty in the depth-of-interaction is comparable to the depth of the crystal array, and is therefore still quite large.

Another disadvantage of the use of scintillator crystals is that the cost of arrays of expensive scintillator crystals has limited PET camera designs to those with small arrays and small geometric coverage, requiring scanning of the patient by a moveable camera, resulting in higher radiation dose and longer exposure time. The large radiation dose inherent in current PET diagnostics renders PET unsuitable for certain patient populations, as well as clinical settings, examples being that the use of PET for children is recommended only for extreme cases, and that PET cameras are found largely in urban hospitals. This significantly limits the prescription of PET as a diagnostic compared to other diagnostic tools, such as X-rays.

Time-of-flight PET (TOF-PET) ameliorates some of these drawbacks by supplying information on the position of the positron (e+)-electron (e−) annihilation by measuring the difference in times of arrival of the resulting gamma rays in the two opposing crystal arrays of the PET camera. This provides more information per event for image processing, allowing a lower dose and exposure. However, a drawback of conventional TOF-PET is that the crystals are typically read out with conventional photomultipliers (PMT's), with an interpolation to achieve spatial resolution comparable to the individual crystal size by using Anger logic. The photomultipliers occupy a substantial volume behind the crystals (away from the patient or source), adding expense and limiting the available geometries for TOF-PET cameras. The required volume typically precludes viewing the scintillator from the front face (toward the patient or source) in a clinical camera.

SUMMARY

TOF-PET detector systems and methods for using the detector systems to image gamma ray-emitting samples are provided. The TOF-PET detectors combine low density scintillator materials, such as liquid scintillator materials, with photodetectors having very high temporal resolution to provide enhanced sample imaging.

One embodiment of a TOF-PET detector system comprises: a sample holder; a first time-of-flight positron-emission tomography camera module; and second time-of-flight positron-emission tomography camera module. The first and second camera modules each comprise: a liquid scintillator material having a front face and a back face; a photodetector located on the front face of the liquid scintillator material; and a second photodetector located on the back face of the liquid scintillator material from the first photodetector. The photodetectors in the camera modules each contain a photocathode, at least one microchannel plate and one or more transmission anodes. In the TOF-PET detector systems, the second time-of-flight positron-emission tomography camera module is configured to face the first time-of-flight positron-emission tomography camera module and is located on an opposite side of the sample holder from the first time-of-flight positron-emission tomography camera module.

One embodiment of a method for imaging a gamma ray-emitting region in a sample comprises the steps of: placing a sample that emits coincident gamma ray pairs between a first time-of-flight positron-emission tomography camera module comprising a first low density scintillator material and a second time-of-flight positron-emission tomography camera module comprising a second low density scintillator material; detecting coincident gamma ray pairs in which the first gamma ray interacts with the first low density scintillator material to produce a plurality of optical photon-emitting Compton Scattering and photoelectric energy deposition events in the first low density scintillator material and the second gamma ray interacts with the second low density scintillator material to produce a plurality of optical photon-emitting Compton Scattering and photoelectric energy deposition events in the second low density scintillator material; and determining source positions for the detected coincident gamma ray pairs. The source positions can be determined by: identifying, on a statistical basis, the first of the plurality of optical photon-emitting Compton Scattering and photoelectric energy deposition events produced in the first low density scintillator material by the first gamma ray of a coincident gamma ray pair; identifying, on a statistical basis, the first of the plurality of optical photon-emitting Compton Scattering and photoelectric energy deposition events produced in the second low density scintillator material by the second gamma ray of the coincident gamma ray pair; and calculating a source position for the coincident gamma ray pair based on the positions of the earliest identified optical photon-emitting Compton Scattering or photoelectric energy deposition events in the first and second low density scintillator materials. An image of the gamma ray-emitting region in the sample can be generated based on the calculated source positions.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
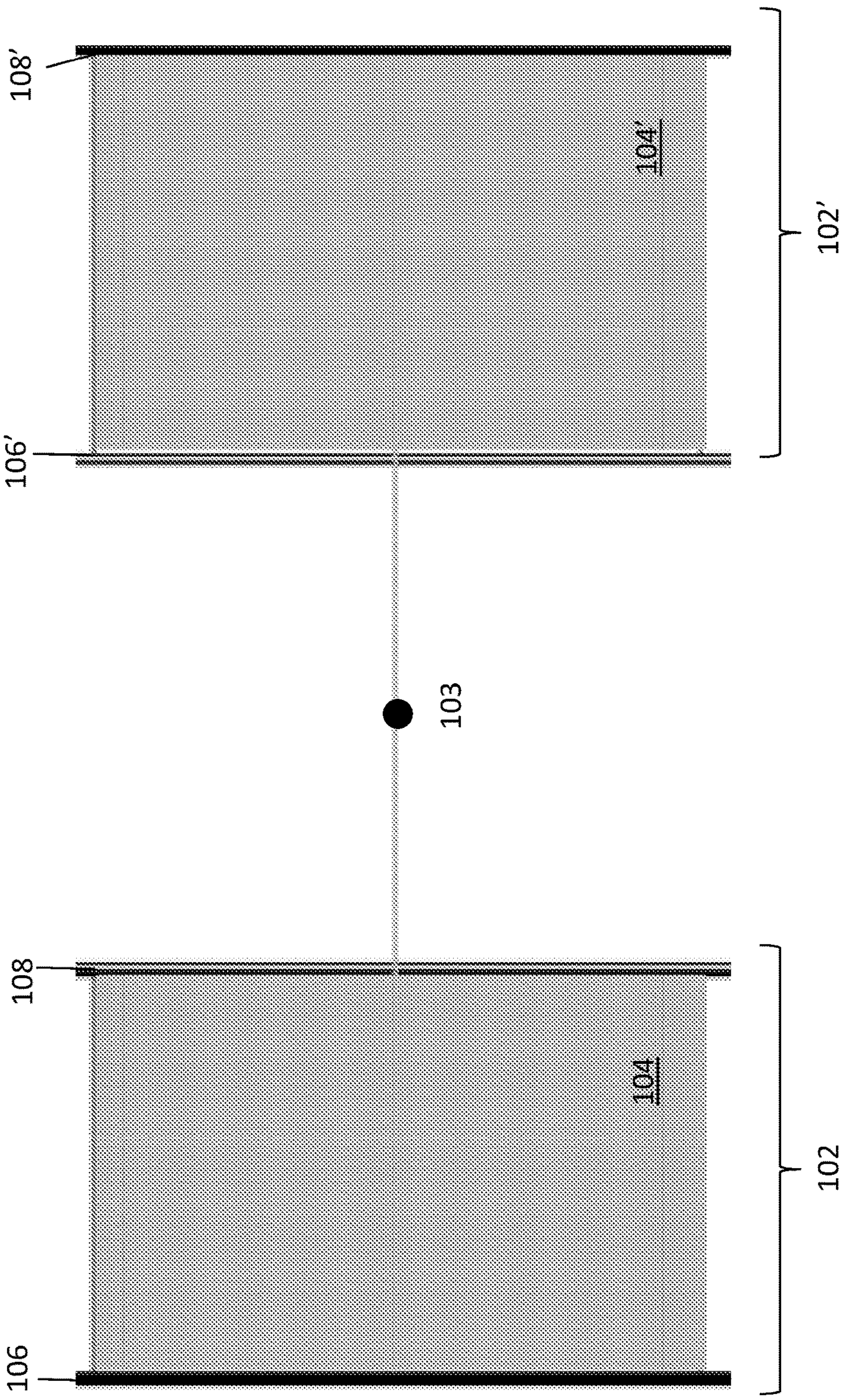
FIG. 1 is a schematic diagram of the basic layout of a TOF-PET detector system.

TOF-PET detector systems and methods for using the detector systems to image gamma ray-emitting samples are provided.

The TOF-PET detector systems use large-area photodetectors with extremely high time-resolution and an approach to data collection and analysis that allows for the use of inexpensive low-density scintillator materials, including water-based and other liquid scintillators, that are unsuitable for use in conventional TOF-PET detector systems. In some embodiments, the liquid scintillator materials are metal-doped. The use of large-area photodetectors in the TOF-PET detector systems allows for an increased geometric acceptance for coincident gamma rays, relative to conventional TOF-PET detector systems, and makes it possible to image a human upper body in a single exposure without moving the photodetectors. As a result, the use of the detector systems in patient imaging is advantageous because it allows for the use of smaller doses of radiation and/or shorter exposure times.

The TOF-PET detector systems are characterized by their ability to resolve the timing and location of individual optical photon-emitting energy deposition events in a series of optical photon-emitting energy deposition events that are generated when a gamma ray interacts with the low-density scintillator material. From these resolved individual optical photon-emitting energy deposition events, the event or events (event(s)) having the highest statistical probability of being the first of the optical photon-emitting energy deposition events in the series can be identified. That is—the first of the optical photon-emitting energy deposition event(s) in the series can be identified on a statistical basis.

The identification of the first of the energy deposition event(s) in the series is accomplished by employing TOF-PET camera modules that include very high resolution photodetectors on opposite sides of the scintillator material. The photodetectors are characterized in that their spatial and temporal resolutions are comparable to or higher than the spatial and temporal separation of the individual energy deposition events in the series. This configuration makes it possible to accurately determine the position of the first energy deposition event(s) on a statistical basis, including the depth of interaction (DOI), within the scintillator material, and to precisely measure the time and position of arrival of the gamma ray. Measuring the time of arrival and the direction of the gamma ray improves the resolution of the 3-dimensional position of the positron-electron annihilation. In addition, geometrical constraints from the time measurements serve to reject background from gamma rays not associated with the annihilation, allowing relaxation of the energy selection criteria used to identify gamma rays. The additional events from the relaxed criteria can be exploited to lower the radiation dose to the patient by using advanced pattern-reconstruction, including real-time event weighting and dynamic pattern recognition The schematic diagram of a basic lay-out of a TOF-PET detector system is depicted in the schematic diagram of FIG. 1. The system components include at least one pair of TOF-PET camera modules, wherein the first camera module 102 of the pair is disposed on one side of a sample holder 103 and the other camera module 102' of the pair is disposed on the opposite side of sample holder 103. Each of the camera modules comprises a low density liquid or gaseous scintillator material 104, 104' positioned between a pair of photodetectors. The pairs of photodetectors each include a front photodetector 106, 106' positioned on the front face of low density scintillator material 104, 104' (that is, the face closer to sample holder 103) and a back photodetector 108, 108' positioned on the back face of the low density scintillator material 104, 104' (that is, the face farther from sample holder 103). It should be noted that the scintillator material may be contained within a housing that separates the photodetector from the scintillator material. Thus, for the purposes of this disclosure, a photodetector is considered to be positioned on a face of a scintillator material even if the photodetector and the scintillator material are separated by a housing and, therefore are not in direct contact.

The camera modules may be configured such that they are able to move relative to a sample in the sample holder in order to change their field of view. Alternatively, they may be in a fixed position relative to the sample.

Figure 2:
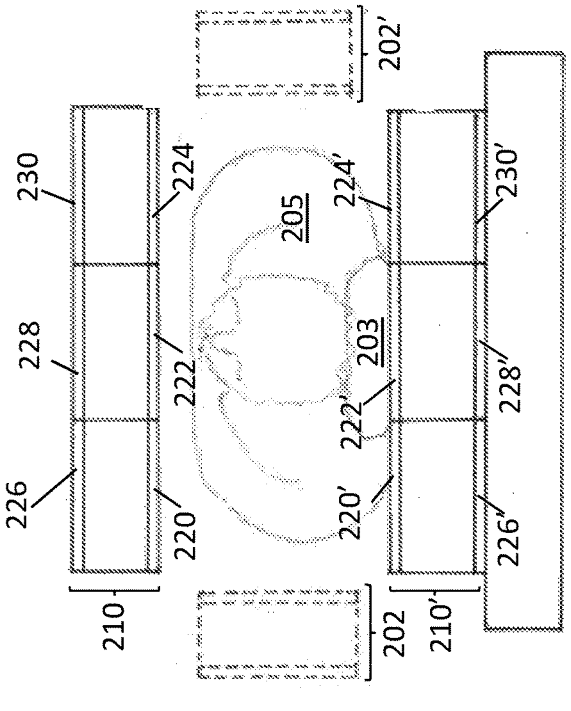
FIG. 2 is a schematic diagram of a TOF-PET detector system with four camera modules around a patient. Each camera module has a front-side and a back-side photodetector. The photodetector shown here is a 3×4 ‘Supermodule’ array.

Although the embodiment of the TOF-PET detector system illustrated in FIG. 1 includes only a single pair of TOF-PET camera modules, multiple TOF-PET camera module pairs can be used. For example, as shown in the schematic diagram of FIG. 2, the TOF-PET detector system can include a first pair of camera modules 202, 202' disposed on opposite lateral sides of a sample holder 203 supporting a human patient (the sample) 205, a second pair of camera modules 210, 210' centered over the anterior and posterior sides of the patient. The frontside and backside photodetectors in camera modules 210 and 210' are Supermodule arrays comprising multiple photodetector tiles 220, 222, 224, 226, 228, 230 and 220', 222', 224', 226', 228', 230'. (Supermodule array photodetectors are discussed in more detail below.)

The sample holder in the TOF-PET detectors is configured to position a sample between the TOF-PET camera modules, typically so that the sample is centrally positioned between the camera modules of each module pair. In some embodiments, the sample holder simply comprises a horizontal platform, such as a table or bed, or a vertical surface against which the sample could be placed. Samples to be imaged with the PET-TOF detector systems include animals, such as a humans or other mammals, and materials or phantoms that simulate the physiology and/or biological composition of such animals. One or more sources of coincident gamma ray pairs is present in the sample to be imaged.

In some embodiments, the source of coincident gamma rays may be generated by positron-emitting radioisotopes ingested, or otherwise taken up, by the sample (e.g., a patient) and localized in a region of interest within the sample. The emitted positrons thermalize in the tissue of the patient, attract an electron, and annihilate to form back-to-back 511 KeV gamma rays (i.e. a pair of gamma rays in traveling 180° for one another). These back-to-back photons, which are referred to as coincident gamma ray pairs, are ideally detected by the photodetectors in the opposing camera modules of a camera module pair.

In other embodiments, the source of coincident gamma rays may be a beam of hadrons, particles that interact strongly with the nuclei of atoms, and which are used in Hadron therapy as a therapy for cancer. In hadron therapy, hadrons deposit energy in a small spot within a patient, the location of which is determined by steering the hadron beam, with the maximum energy deposited at a depth in the sample determined by the energy of the beam. Thus a three-dimensional volume, such as a tumor, can be irradiated and destroyed by the beam by steering and by energy control. A PET detector system, and especially a high-resolution TOF-PET detector system, can supply much-needed real-time feedback on the position of the beam. As positrons are created in the patient by the beam they annihilate with electrons to form back-to-back gamma rays. Like the back-to-back gamma rays generated by positron-emitting radioisotopes, the gamma rays generated by the hadron beam can be detected by the photodetectors in the opposing camera modules of a camera module pair.

The photodetectors in the TOF-PET detector systems desirably have sub-nanosecond (nsec) time resolutions and spatial resolutions of a few millimeters (mm) or better. For example, some embodiments of the photodetectors have time resolutions of 40 picoseconds (psec) or better and spatial resolutions of 1 mm or better for single photons. The time resolution values recited herein are quoted in sigma and not FWHM. FWHM time resolution ≈2.3 sigma resolution. This includes embodiments of the photodetectors having time resolutions of 20 psec (sigma), or better, for a single photon and further includes photodetectors having time resolutions of 10 psec (sigma), or better, for a single photon. Resolutions can be significantly better for larger numbers of photons.

Suitable photodetectors include the substantially planar, large-area, flat-panel photodetectors with sub-nanosecond time resolution described in U.S. Pat. No. 8,604,440, the entire disclosure of which is incorporated herein by reference. These photodetectors can have time resolutions of 50 psec or better and spatial resolutions of 1 mm or better. These photodetectors comprise: a photocathode that absorbs photons and emits electrons; at least one microchannel plate that amplifies the emitted electrons; and one or more transmission (signal collecting) anodes that collect the charge constituting the electrical signal. The anodes may be transmission line anodes comprising electrically conducting strips or discrete pixel anodes comprising individual electrically conducting pads. These photodetectors may further include sampling electronic circuitry in communication with the one or more anodes, (for example, if the anodes are transmission line anodes, the sampling circuitry may be connected at one or both ends of each of the one or more transmission line anodes), electronics connected to individual anode pixels (i.e., contact pads) on the non-vacuum side of the anode plate, and an additional electronic circuit connected to the sample electronic circuitry. For example, if transmission line anodes are used the additional electronic circuit can be adapted to determine the distance along the transmission line anode at which electron collisions with the transmission line anode occur. Additional electronic circuitry can be connected to the pair of photodetectors in a camera module and adapted to detect a pair of coincident gamma rays emanating from a sample.

Figure 3:
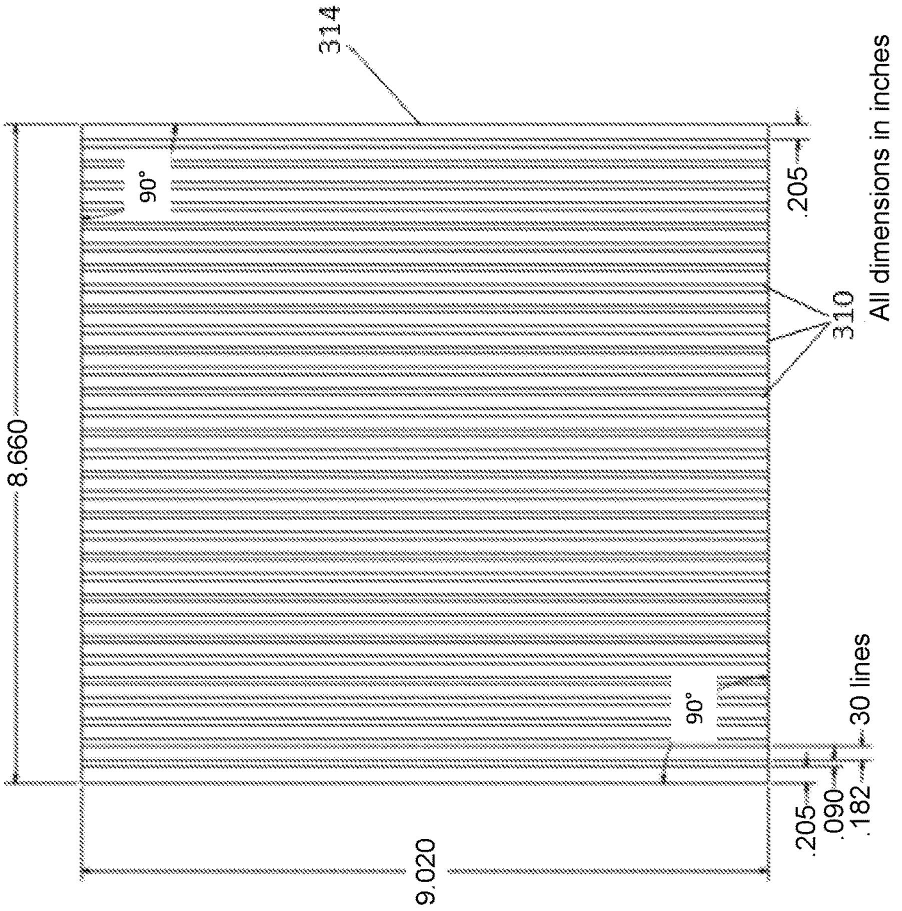
FIG. 3 shows a typical layout for transmission line anodes in a large-area, flat-panel photodetector.
Figure 4:
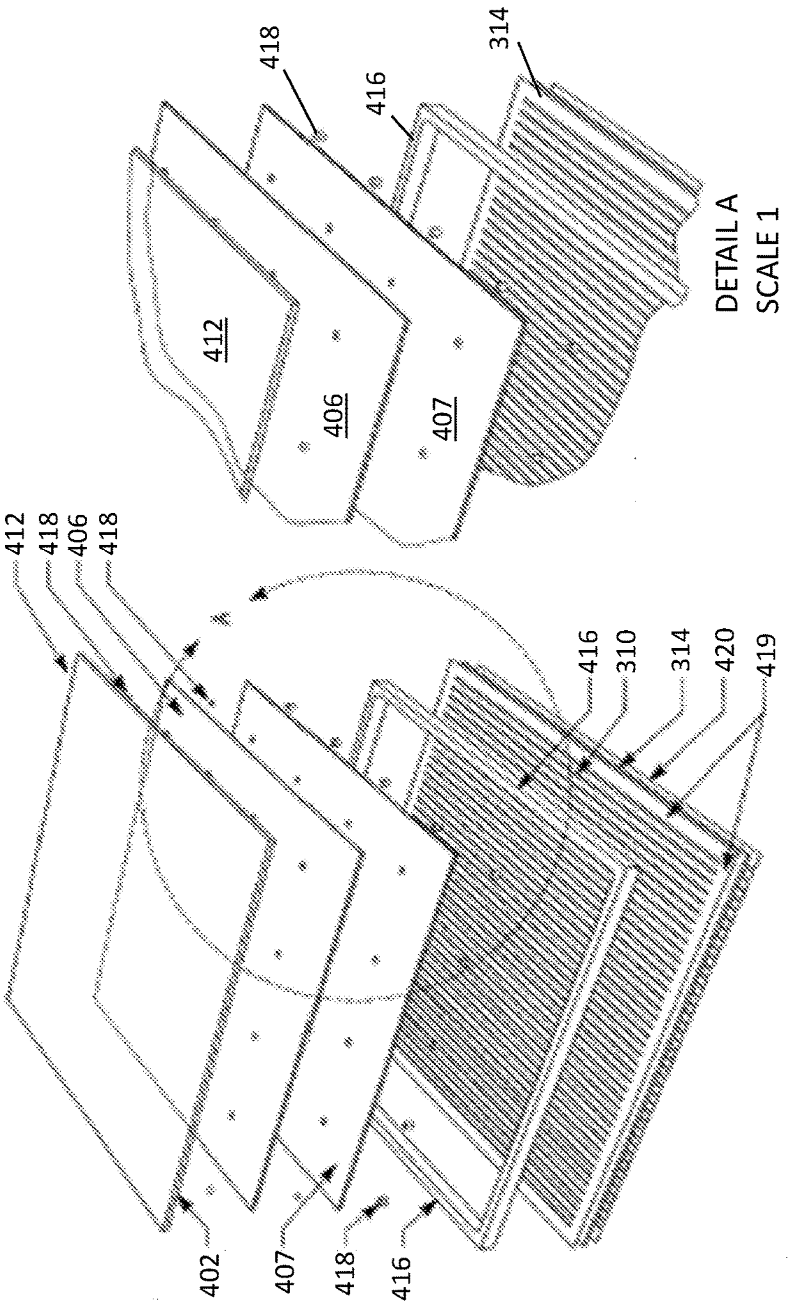
FIG. 4 is a schematic diagram of the component pieces of a typical large-area, flat panel photodetector incorporating the transmission line anodes of FIG. 3.

FIG. 3 shows a typical layout for the transmission line anodes 310 on a dielectric base plate 314 in a photodetector comprising a plurality of the transmission line anodes. The dimensions provided in the figure are intended to be illustrative. Other dimensions can be used. FIG. 4 shows an exploded view of a photodetector comprising a pair of adjacent microchannel plates 406 and 407 disposed between a photocathode 402 and the transmission line anodes 310 of FIG. 3. Microchannel plates 406, 407 make up the amplification section of the photodetector. Photocathode 402 is disposed on the inner surface of a transparent substrate, such as a fused-silica plate (window) 412. Photocathode 402 could also be disposed on the front face of microchannel plate 406. A frame 416 separates base plate 314 and its transmission line anodes 310 from lower microchannel plate 407. In the embodiment shown here, a sidewall seal surface 419 is formed around the perimeter of base plate 314. Spacers 418, shown in one embodiment as discrete elements, separate microchannel plates 406 and 407 from one another and upper microchannel plate 406 from photocathode 402.

In the embodiment of the photodetector shown in FIG. 4, base plate 314 further includes a bottom transmission line pattern comprising a plurality of transmission line anodes 420 on its lower surface. Together, window 412, frame 416 and base plate 314 form a vacuum volume. (An alternative design, the "inside-out" configuration, is described in detail in US 2011/0220802.) The top transmission line anodes 310 are shorted and connected to ground. Alternatively the top transmission anode may comprise a single anode that covers the whole surface. The bottom transmission line anodes 420 lie outside of the vacuum and are coated onto a printed circuit board (PCB), which is brought into contact with base plate 314. (Although the bottom anodes in this embodiment of the photodetector are line anodes, they could also be discrete pixel anodes.) The anode inside the vacuum provides a DC connection for the "ground" side of the signals, while at RF frequencies the transmission lines function independently as the top traces of transmission line pairs or, in the case of discrete pixel electrodes, as the signal side of a pair leading to an electronic readout.

Transmission line readout electronics are present for waveform sampling of the electric signal on the signal transmission lines (relative to the aligned grounded transmission lines). The electrical signals are digitized at one or more ends of the transmission line anodes. Signal digitization by waveform sampling chips can be used for a precise measurement of the time of arrival, amplitude, shape, and integrated charge for each pulse at both ends of a transmission line anode. Typical propagation velocities for signals along the transmission lines are in the range from 0.2 to 0.3 mm/psec. From these data, one can reconstruct the position of a pulse along the transmission line from the difference in the times at the two ends, and the time of the pulse from the average of the two times. The position in the direction orthogonal to the transmission lines is given by the amplitude distribution among the transmission lines.

The photodetector shown in FIG. 4 comprises a single photodetector tile. However, the photodetectors in the TOF-PET detector systems may comprise a plurality of such tiles in which the tiles are connected in a planar array so that the transmission line anode termini of each tile are in electrical contact with the transmission line anode termini of adjacent tiles to form "Supermodule arrays", such that the transmission line signal readout is implemented at the free transmission line anode termini but not necessarily at the contacting termini at the adjacent tile interface. Supermodules are scalable, in that m×n Supermodule arrays may be prepared, where m is equal to or greater than one and n is equal to or greater than one.

In the case that the 'inside-out' configuration is implemented with discrete pixel electrodes, similar readout electronics as in the transmission line embodiment above are present to digitize the signals. In this embodiment, the position is determined by the charge on one or more of the pixels, with interpolation possible from charge-sharing.

Figure 5B:
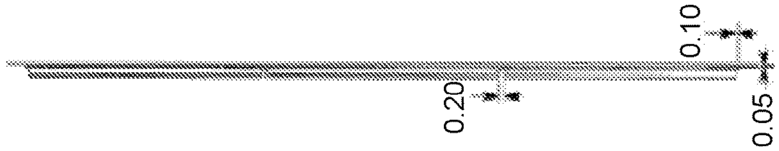
FIG. 5B. Schematic diagram showing a side edge view of the Supermodule array of large-area, flat panel photodetector tiles.
Figure 5A:
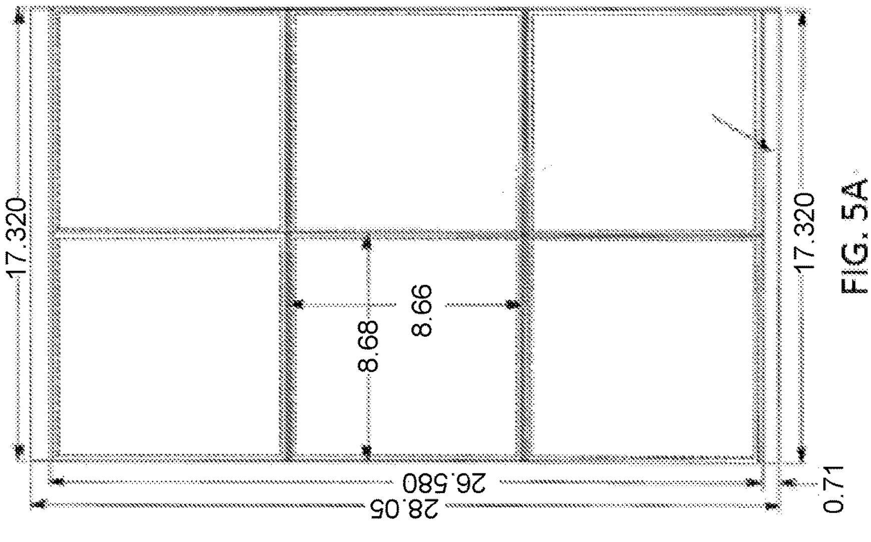
FIG. 5A. Schematic diagram showing a front view of a Supermodule array of large-area, flat panel photodetector tiles.
Figure 5C:
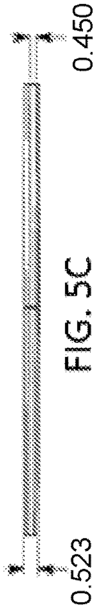
FIG. 5C. Schematic diagram showing a bottom edge view of the Supermodule array of large-area, flat panel photodetector tiles. Supermodules can comprise arrays with different numbers of rows and columns of detector modules, such as 2×3, 3×4, using the same mechanical design and the same readout electronics.

One embodiment of a Supermodule array is shown in FIGS. 5A, 5B, and 5C. This Supermodule array comprises six photodetector "tiles" 500 in a 2×3 array of large-area, flat panel photodetector tiles, forming a unit with a photosensitive area of 24"×16". The tiles may be fastened with an adhesive, including but not limited to, a light glue or double-sided tape, onto a tray that contains the bottom transmission line anodes, which run the length of the tray. The tiles are connected across the inter-tile gaps and digitization electronics may be provided on the ends of the columns. In this embodiment, on each end of each chain of transmission line anode base plates a printed-circuit card contains five 6-channel psec ASICs. This card is connected by a mechanical interface, spot-welding, solder, or other conducting material, onto the anode substrate, picking up and continuing the anode transmission lines directly into the 50-ohm inputs of the front-end ASICs. A second printed-circuit card that contains the FPGA for front-end control and data-reduction, a jitter-cleaner chip, and the optical fiber interface, controls and collects data from the first cards. The number of tiles, dimensions and array geometries shown in FIGS. 5A-5C are for illustration only. Other tile numbers, dimensions and array geometries can be used. For example, an embodiment of a TOF-PET detector system for a whole body scan of a human subject may include Supermodules with a 3×4 array of photodetector tiles.

Within each camera module, photodetectors are arranged on opposing sides of a low density scintillator material and configured to detect optical photons generated in the low density scintillator material. The low density scintillator materials typically have densities of no greater than about several kg/L at the temperature at which the TOF-PET is operated, typically room temperature (~23° C.). The low density scintillator materials may be, for example, liquids or gases. The optical photon-emitting energy deposition events detected by the photodetectors arise from two types of fundamental processes that govern the interaction of a gamma ray with the scintillator material: Compton Scattering and the Photoelectric Effect. Compton Scattering and the Photoelectric Effect are illustrated schematically in FIG. 6, which shows an illustration of the treatment by the simulation of deposition of energy in a scintillator material 604 by an incident gamma ray 602 generated by a positron-electron annihilation in a sample to the left of the figure [not shown]. In this illustrative example, the incident gamma ray Compton scatters at location A, producing an electron which deposits energy on the path between A and B. The gamma ray, now at a lower energy after the collision 606 so that the photoelectric cross-section is larger, deposits energy by the Photoelectric Effect at location C, with a secondary electron that additionally deposits energy along the path between C and D.

Figure 6:
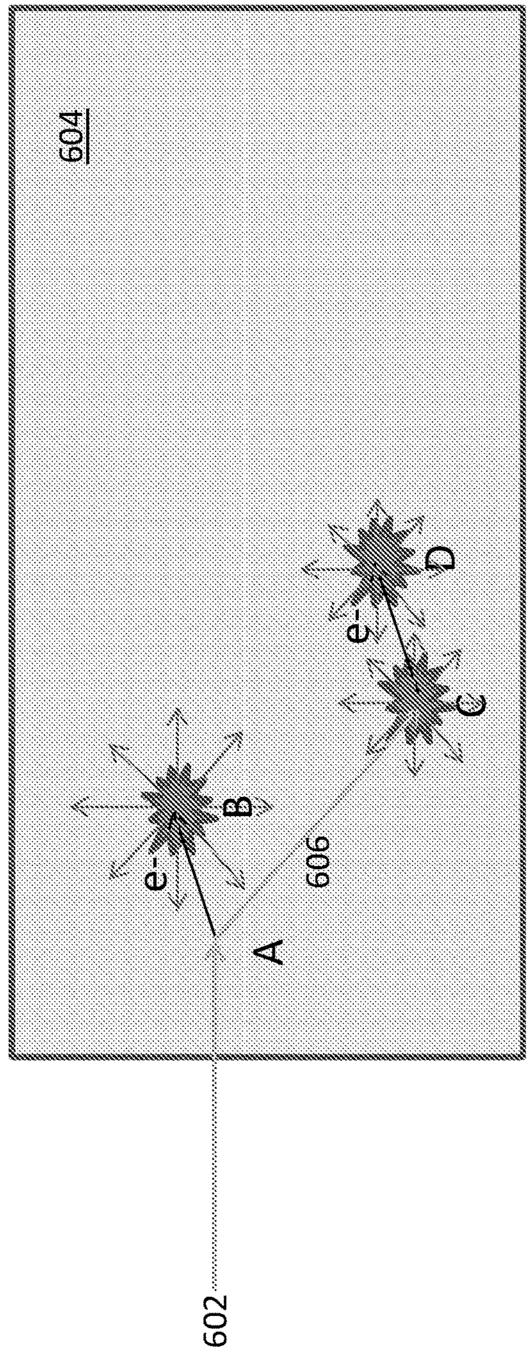
FIG. 6 is an illustration of the treatment by the simulation of deposition of energy in a scintillator material by an incident gamma ray generated by a positron-electron annihilation in a sample to the left of the figure (not shown).
Figure 7:
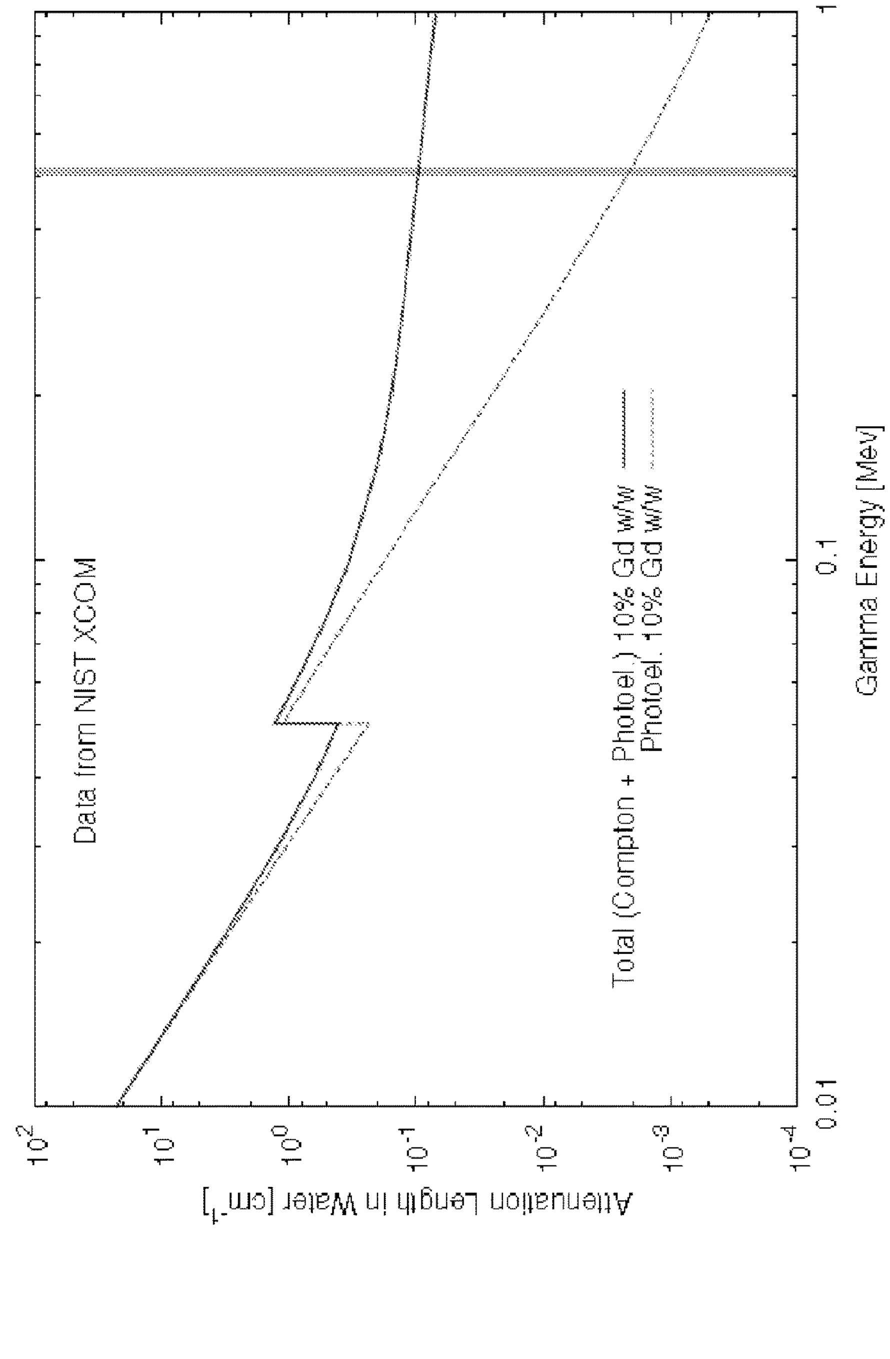
FIG. 7 is a graph showing the Photoelectric Effect and Compton Scattering cross-sections versus gamma ray energy for a water-based scintillator material with a 10% concentration of the heavy element Gadolinium. The vertical gray line at 511 KeV represents the initial energy of the gamma rays from positron-electron annihilation.

A large Compton Scattering cross-section provides a high detection efficiency by lowering the energy of the gamma ray into the region of a large photo-electric cross-section. Therefore, elements with an atomic number greater than that of oxygen (atomic number Z=16), such as Gadolinium (Z=64), may be included as "high-Z elements" in the scintillator materials to provide a high Compton Scattering cross-section. The relationship between Compton Scattering cross-section and energy absorption efficiency is illustrated in FIG. 7, which shows the Photoelectric Effect and Compton Scattering cross-sections for gamma rays interacting in a water-based liquid scintillator. The depth of the scintillator material is desirably substantially greater than the attenuation length. By way of illustration only, the scintillator material may have a depth that is about 2 to about 3 times greater than the attenuation length of a 511 KeV gamma ray in the scintillator material. However, as shown in FIG. 6, the depth of the scintillator for any given detector system will depend on the nature of the scintillator material.

The high-Z elements can be introduced into a liquid-based low density scintillator material by dissolving salts or other compounds of high-Z materials in the liquid. An example of a suitable liquid-based scintillation material is a Gadolinium-loaded liquid-based scintillator, a description of which can be found in Lightfoot et al., Nucl. Instr. And Meth. A522, 439 (2004). Other descriptions using different chelating-ligand or water-based loadings can be found in Beriguete, et al. Production of Gadolinium-loaded Liquid Scintillator for the Daya Bay Reactor Neutrino Experiment; e-Print: arXiv:1402.6694 (Feb., 2014); Minfang Yeh, Liquid Scintillator Challenges for Physics Frontiers, RENO 50, SNU, Korea, Jun., 2013; Yeh et al., A new water-based liquid scintillator and potential applications; Nucl. Instrum. Meth. A660, 51-56 (2011); and A. G. Piepke et al.; Development of a Gd loaded liquid scintillator for electron anti-neutrino spectroscopy; Nucl. Instrum. Meth. A432, 392-398 (1999). However, a variety of liquid scintillators comprising different high-Z elements (e.g., Lead), photoactive solutes and liquids may be used. (See, for example, M. Yeh, Water-based Liquid Scintillator and Isotope Loading, NNN, Paris, France (2014)).

Unlike the present systems, conventional TOF-PET detection systems rely upon high density solid crystal scintillator materials in order to promote the absorption of the total energy from an incident gamma ray efficiently and in a very small volume of the scintillator. This allows for the use of relatively small scintillators, which provide a higher spatial resolution. In contrast, in the present TOF-PET detector systems, low density scintillators are used to allow the energy deposition events, through which the energy of the incident gamma ray is deposited in the scintillator, to occur with large spatial separations within a relatively large volume. Notably, because a lower density scintillator material increases the ratio of event separation to detector resolution, lower densities make it possible statistically to identify the position of the first of the deposition events. This enhances the imaging capabilities of the TOF-PET detector systems.

The imaging of a sample using the present TOF-PET detector systems is carried out by placing a sample that emits coincident gamma ray pairs between a pair of the TOF-PET camera modules. The first and second gamma rays of the pair arrive at the first and second TOF-PET camera modules, respectively, within a given coincidence detection window (for example, within 50 psec of one another). Both gamma rays travel at the velocity of light in vacuum in the scintillator material. The first and second gamma rays, which behave as particles in the low density scintillator material, interact with that material in the first and second TOF-PET cameras, respectively, to produce a plurality of optical photon-emitting Compton Scattering energy deposition events and photoelectric energy deposition events ("Photoelectric Effect" events) in those materials. The wavelengths of the optical photons are long relative to the spacing of the atoms in the scintillator material and, therefore, the photons act as waves in the material, travelling at less than the speed of light in vacuum. The position of the source of each gamma ray pair ("the gamma source position") is determined by identifying, on a statistical basis, the first (earliest) optical photon-emitting energy deposition event(s) in the scintillator materials of opposing TOF-PET camera modules. The positions, including depths of interaction, of the identified first energy deposition events within each of the scintillator materials can be used to calculate a statistically probable (e.g., 1σ and 2σ) volume for the site of the positron/electron annihilation in the sample (the gamma source position) based on a straight line connecting the identified first energy deposition events and intersecting the sample (a line of response; LOR). An image of the gamma photon-emitting region in the sample is then generated based on the calculated gamma source positions. In some embodiments of the method, the calculated gamma source positions have uncertainties of no greater than 1 mm in any direction.

The statistical confidence in the identification of the first in the series of energy deposition events through which a gamma ray deposits its energy in the scintillator material will depend, at least in part, on the nature and number of the events in the series. Therefore, a weighted value may be assigned to the identified first energy deposition event(s) (and/or to the gamma source positions calculated from those events) to reflect their statistical confidence, wherein events (and/or gamma source positions) having a higher statistical confidence are assigned a higher weight and, as a result, are represented with a higher intensity and/or higher contrast in the images constructed from the data.

Methods for determining, on a statistical basis, the position of the first of a series of optical photon-emitting energy deposition events in a scintillator material and methods of determining the gamma source position from those events are described in the Example below.

In order to carry out the data acquisition and imaging functions, the TOF-PET detector system may include a processor and a computer-readable medium operably coupled to the processor. The computer-readable medium has computer-readable instructions stored there that, when executed by the processor, carries out the following steps: (1) identifies, on a statistical basis, the position of the first of a plurality of optical photon-emitting Compton Scattering and Photoelectric Effect energy deposition events resulting from an interaction of the first gamma ray of a coincident gamma ray pair with the first low density liquid or gaseous scintillator material; (2) identifies, on a statistical basis, the position of the first of a plurality of optical photon-emitting Compton Scattering and Photoelectric Effect energy deposition events resulting from an interaction of the second gamma ray of the coincident gamma ray pair with the second low density liquid or gaseous scintillator material; and (3) calculates the gamma source position for the first and second gamma rays based on the positions of the identified first optical photon-emitting Compton Scattering or Photoelectric Effect energy deposition events in the first and second low density liquid or gaseous scintillator materials.

In addition to providing more accurate source position information, the present TOF-PET detector systems are able to utilize more of the data generated by a sample by including gamma rays having energies outside the 511 KeV energy window in the analysis. In a conventional TOF-PET detector system the information from these events is not utilized. However, in some instances a true coincident pair will include one gamma ray with an energy of 511 KeV and a second gamma ray with less than the full energy. This can happen, for example, due to detector related effects. In the present TOF-PET detector systems, the precise timing of both gamma rays in a coincident pair can be used to identify true coincident pairs with a very high probability, given that both gamma rays in a pair travel at velocity c, even in the scintillator medium. As a result, the requirement on energy resolution can be relaxed, as there is additional background suppression from the time constraint. This relaxation in the energy requirement provides an opportunity to use data generated by gamma pairs that have one gamma in the 511 KeV peak (referred to here as ‘Gold’ gammas) and one that deposits some energy but less than the full energy in the scintillator material (referred to here as a ‘Silver’ gamma). The information content of the events with Silver gammas grows as the image is formed. Therefore, given the time and position of the energy deposition(s) of the Gold gamma and the Silver gamma, a weighted map of probabilities can be constructed, wherein the weight assigned to a given coincident gamma ray pair is a function of the gamma ray energies, their angles and path lengths through the sample, and the detector resolutions. The requirement for the data generated by a gamma ray pair that includes one gamma ray outside of the 511 KeV peak is that the signal-to-noise for the data generated from that pair be greater than the cumulative signal-to-noise in the developing image of the gamma ray-emitting region of the sample.

Including gamma rays outside of the 511 KeV peak increases the efficiency of the TOF-PET system and, therefore, reduces the dose of radiation needed for a given level of precision. For example, in a plausible scenario where out of 5000 events at the gamma source only about half of them have both gammas interact with two opposing cameras and, of those, only about 25% have both gamma rays in the 511 KeV band, then only about 12% of the initial 5000 gamma ray pairs are being analyzed. If silver gamma rays are included in the data, the number of gamma ray pairs being analyzed could be increased by at least a factor of three, allowing for a significant decrease in the radiation dose.

By way of illustration only, under one weighting scheme, weighted values would be assigned to the gamma source positions for the coincident gamma ray pairs based on the deposition energies of their first and second gamma photons, such that gamma source positions calculated from coincident gamma ray pairs in which both gamma rays have deposition energies inside the 511 KeV energy peak have a higher weighted value than the source positions for coincident gamma ray pairs in which one of the gamma rays has a deposition energy outside the 511 KeV energy peak. The more heavily weighted source position data points can then be depicted with higher intensities and/or contrast in an image of the sample. In some embodiments of the weighing scheme, gamma rays having energies below a preselected threshold (for example, below 100 KeV) can be excluded from the data and the image generated therefrom. The weighing schemes need not be static, but can evolve dynamically as more source position data is acquired and the signal-to-noise ratio in the developing image increases. Thus, the weighted values of the source positions could be periodically revised based on their proximity to other source positions, such that source positions close to other source positions have a higher revised weighted value than source positions that are not close to other source positions. The image of the sample can then be revised to reflect the revised weighted values of the source positions.

EXAMPLE

This example illustrates one method for identifying the location of the first optical-photon emitting energy deposition event in a series of such events within a low density liquid scintillator material and for identifying the location of the gamma ray source within a sample from the location of the of the first optical-photon emitting energy deposition event. This example is based on a simulation of the optical photons inside a water based scintillator material. The simulation was carried out using a Geant4 package. A description of this type of simulation can be found in Kim et al., *Nucl Instrum Methods Phys Res* A. 2010; 622(3): 628-636. In the present example, the simulation was modified for a liquid based scintillator. The method is described in conjunction with FIGS. 8-16, which are described below.

Figure 8:
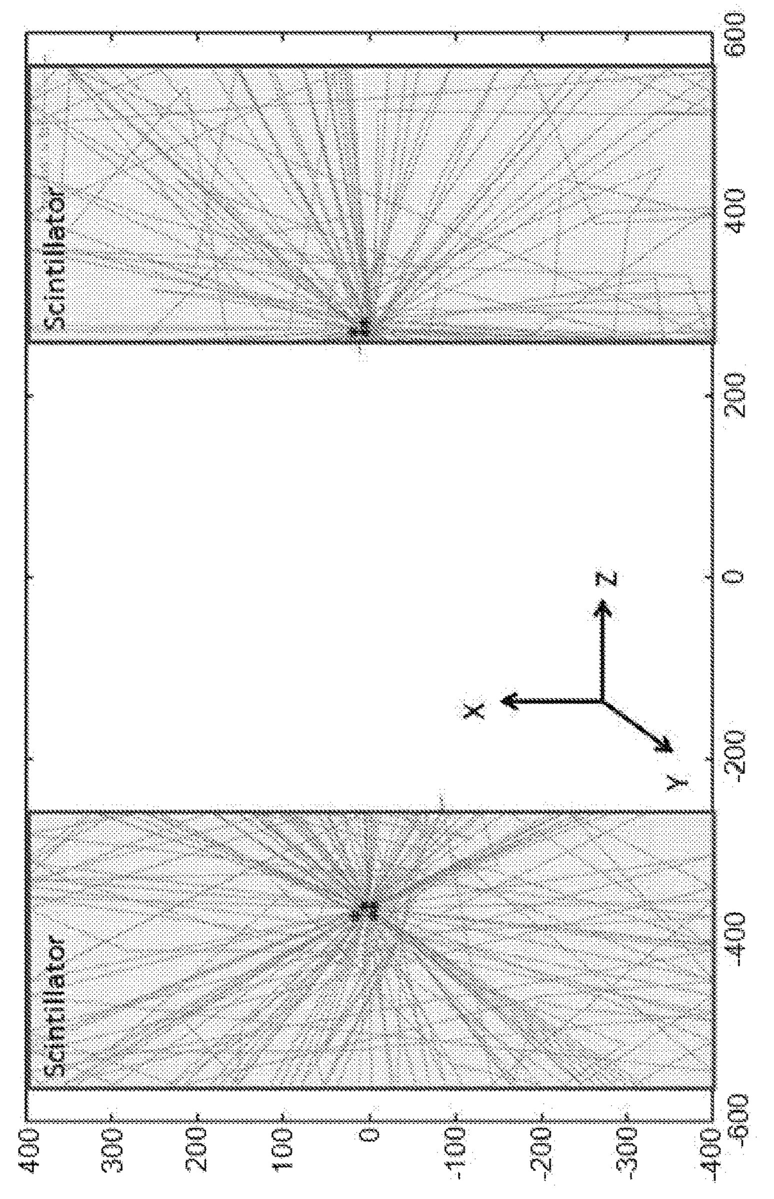
FIG. 8 shows the GEANT 4 simulated trajectories of optical photons generated by Compton Scattering and Photoelectric Effect events in two opposing TOF-PET camera modules. The scintillator material is Water-based Liquid Scintillator (WbLS) loaded with Gadolinium at 10% by weight. The scales on the axes are in mm.

FIG. 8 shows the GEANT 4 simulated trajectories of optical photons generated by Compton Scattering and Photoelectric Effect events in two opposing TOF-PET camera modules. The simulated medium is water-based liquid scintillator (WbLS) loaded with Gadolinium at 10% by weight. The scales on the axes are in mm.

Figure 9:
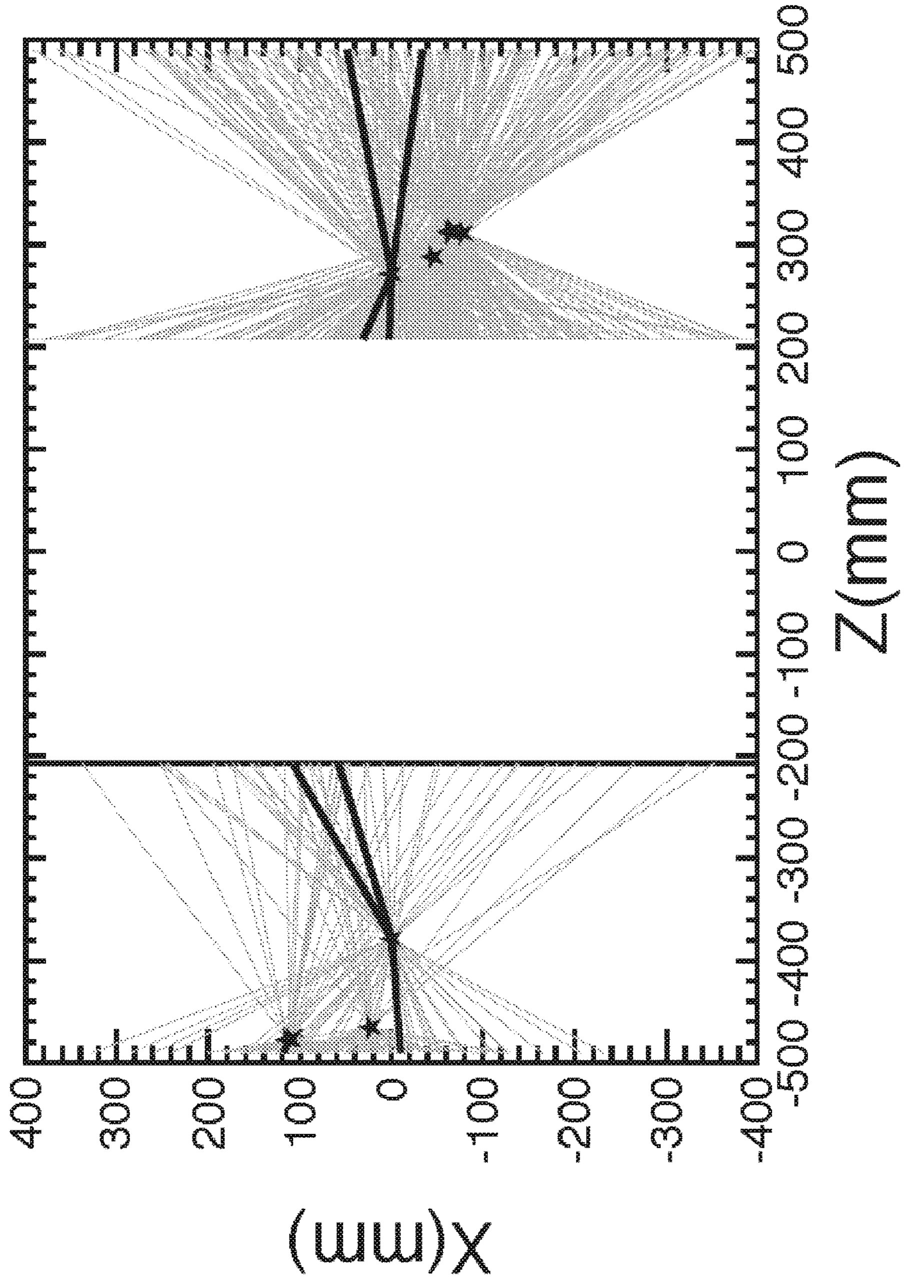
FIG. 9 shows, in a single event, the simulated trajectories of optical photons generated by Compton Scattering and Photoelectric Effect events in two opposing TOF-PET camera modules, where the optical photons are shaded based on their time of arrival at the photodetector.

FIG. 9 shows, in a single event, the simulated trajectories of optical photons generated by Compton Scattering and Photoelectric Effect events in two opposing TOF-PET camera modules, where the optical photons are shaded based on their time of arrival at the photodetector. Only photons arriving within 5 nsec of the positron annhilation are shown. The black stars represent sites of energy deposition, with the density of rays proportional to the magnitude of the energy. The earliest depositions in a given photodetector are statistically more likely to emanate from an early interaction of the gamma ray, allowing a determination on a statistical level of the initial gamma ray direction. The first two optical photons arriving at each of the front and back faces of each of the two modules are shown as thicker, darker solid lines. Additional vertices can add information to the direction determination.

Figure 10:
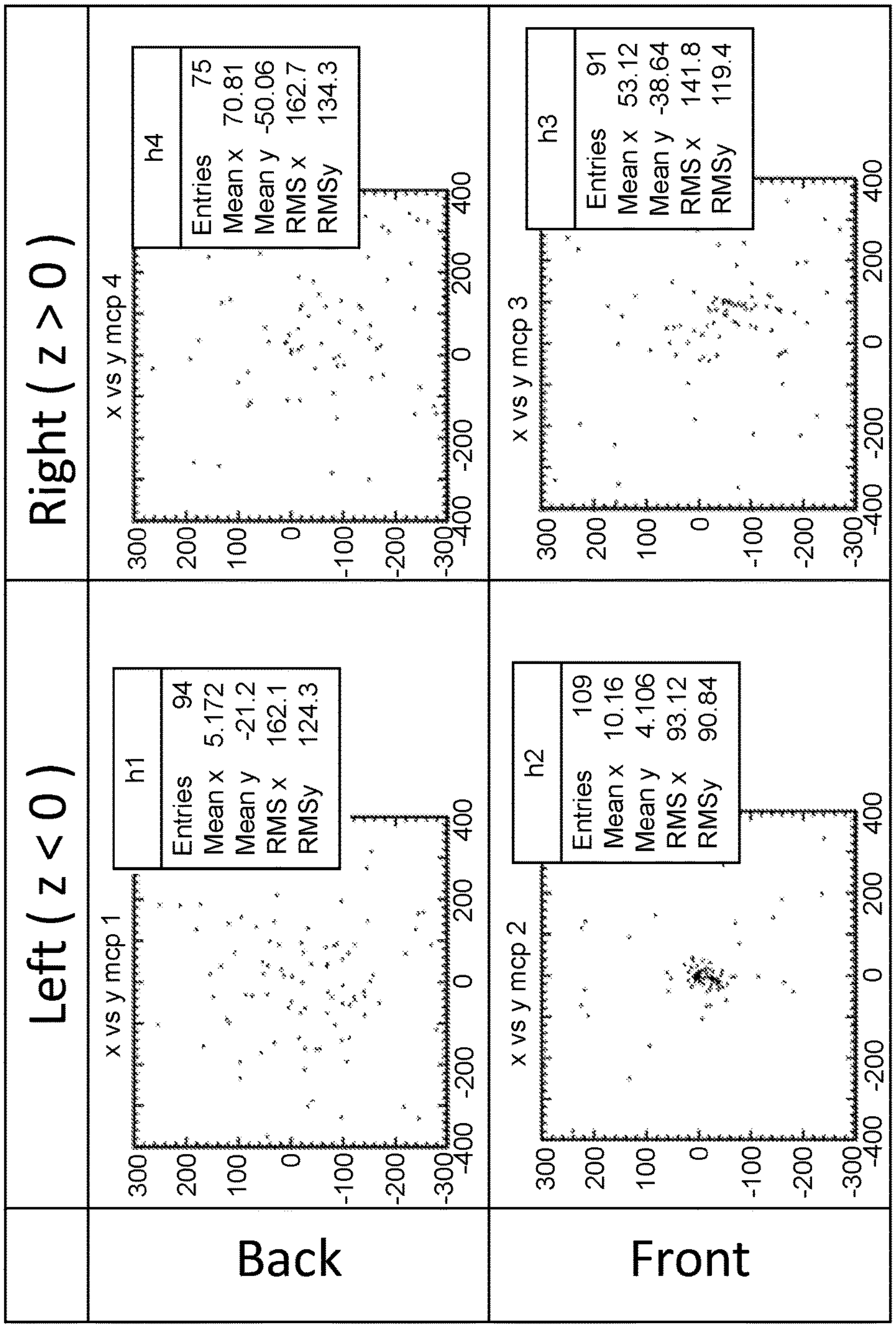
FIG. 10 shows the simulated distribution of optical photons arriving at the back and front faces of two (Left and Right) opposing TOF-PET camera modules in a single event.

FIG. 10 shows the simulated distribution of optical photons arriving at the back and front faces of two (Left and Right) opposing TOF-PET camera modules in a single event. For each panel the x-axis is the horizontal border of the photodetector and the y-axis is the vertical border. The top row of panels shows the distribution in the Left and Right rear (away from the source) detectors; the bottom row shows the corresponding distributions in the front detectors.

Figure 11A:
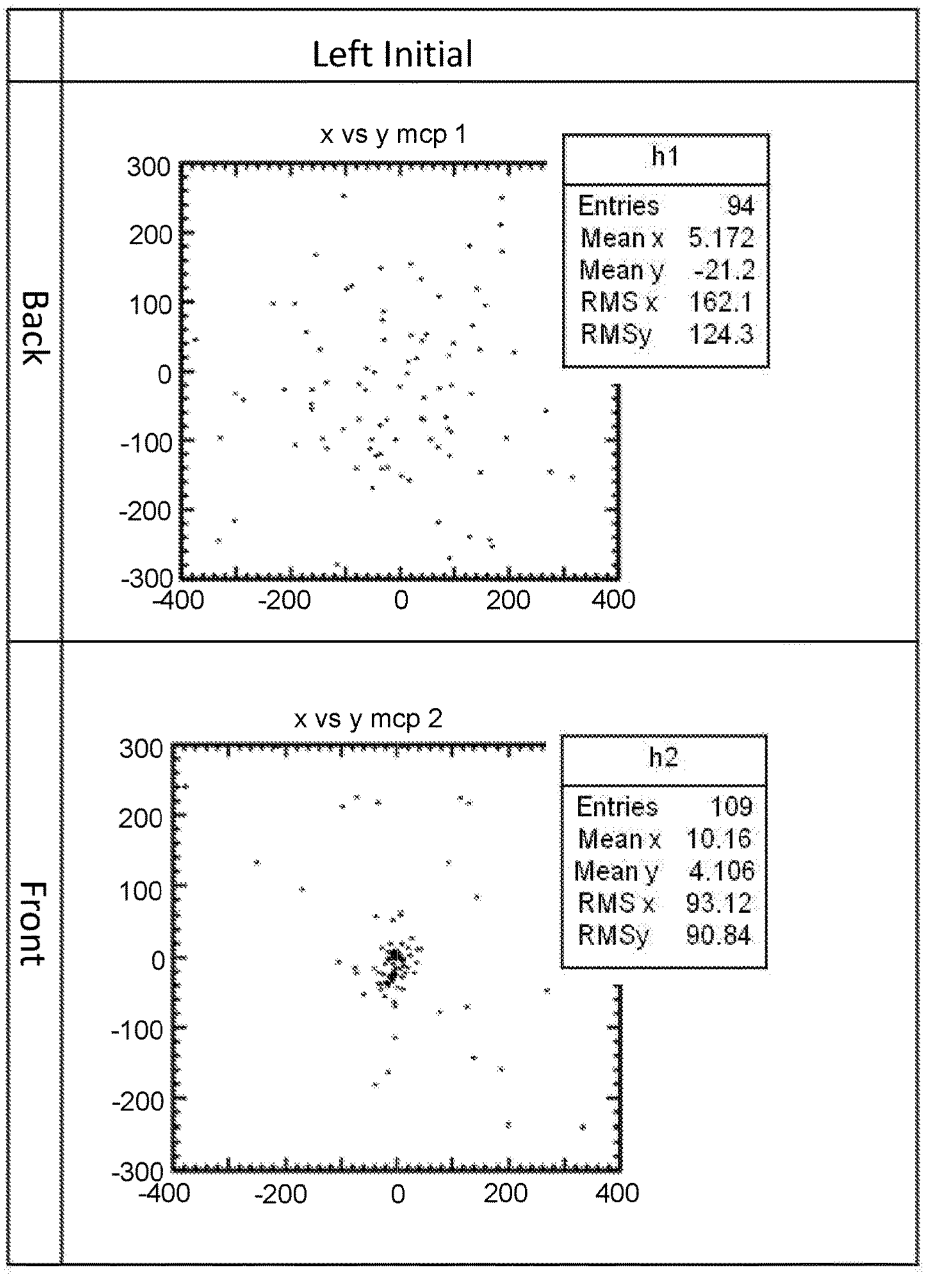
FIG. 11A shows the simulation distribution of optical photons arriving at the back (top panel) and front (bottom panel) faces of a TOF-PET camera module, without a time-of arrival filter.
Figure 11B:
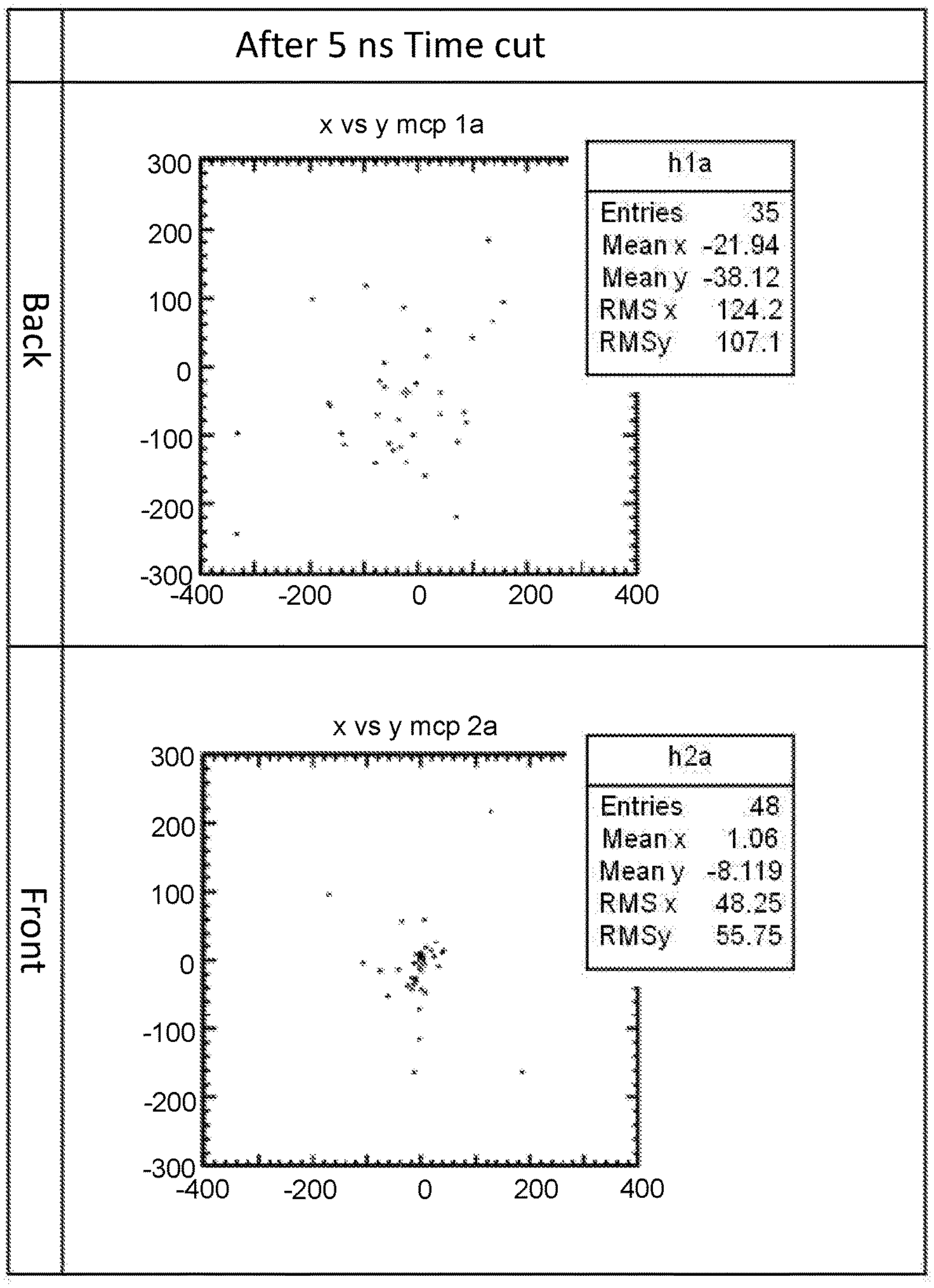
FIG. 11B shows the simulation distribution of optical photons arriving at the back (top panel) and front (bottom panel) faces of the TOF-PET camera module after a 5 nsec time cut.
Figure 11C:
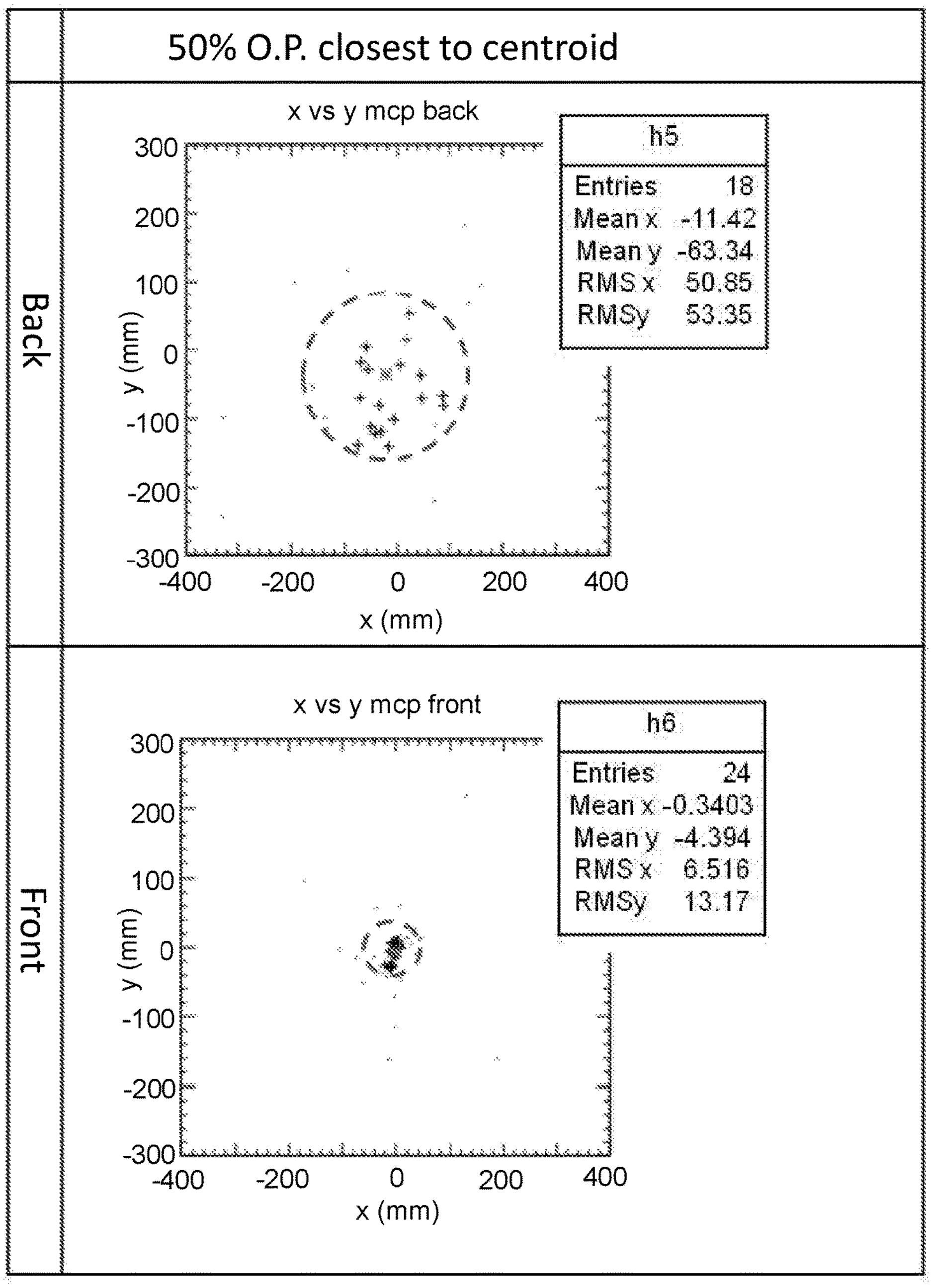
FIG. 11C shows the simulation distribution of optical photons arriving at the back (top panel) and front (bottom panel) faces of a TOF-PET camera module limited to the 50% of the photons lying closest to the centroid of the distribution.

FIG. 11 shows the simulation distribution of optical photons in a single event arriving at the back (top panel) and front (bottom panel) faces of a TOF-PET camera module, without a time-of arrival filter (FIG. 11A), after a 5 nsec time cut (FIG. 11B) and limited to the 50% of the photons lying closest to the centroid of the distribution (FIG. 11C).

Figure 12A:
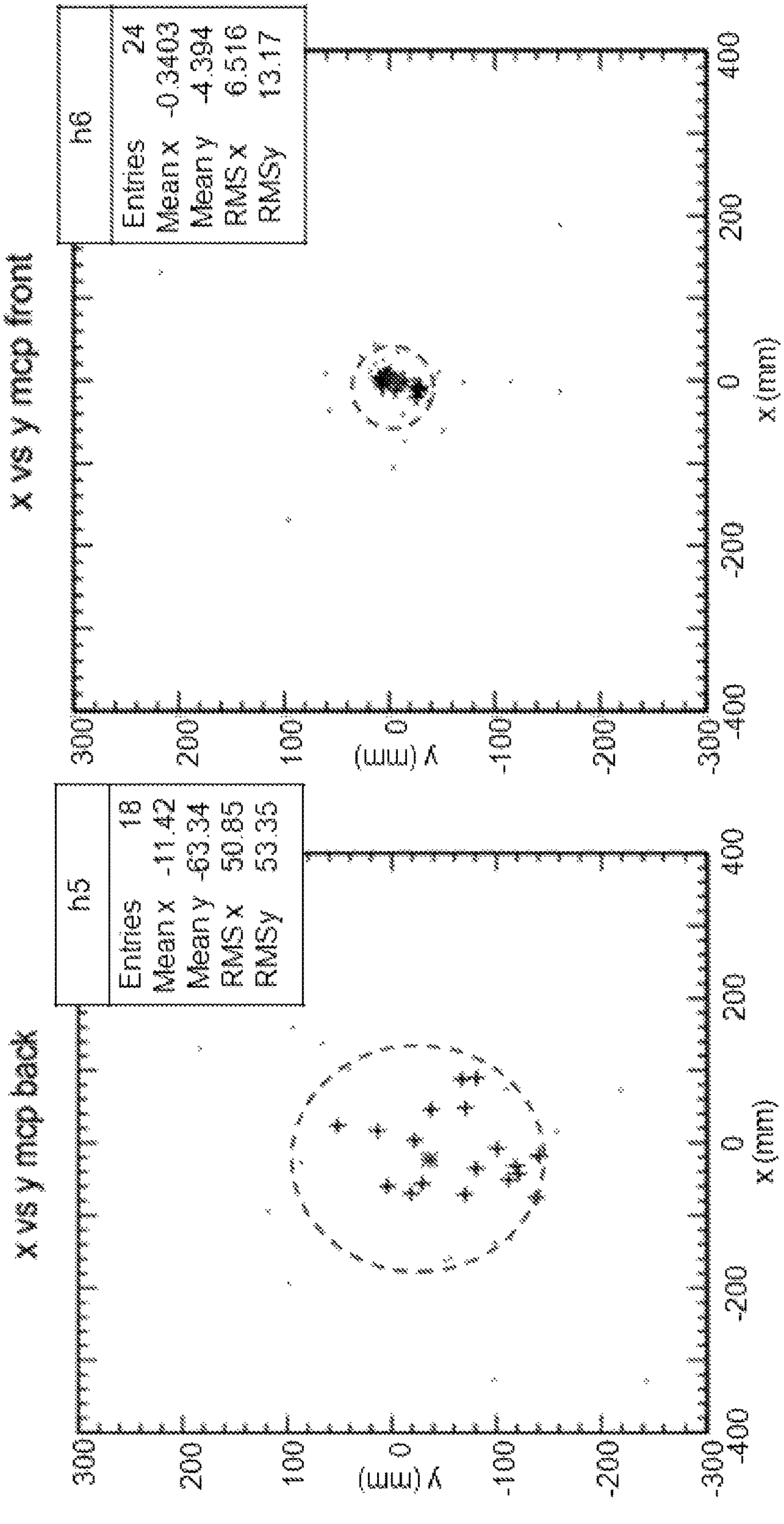
FIG. 12A illustrates the first step in one embodiment of an algorithm for determining the longitudinal and transverse positions of the first energy deposition event in a scintillator material based on the distributions of the optical photons on the faces of the scintillator.

FIG. 12A illustrates the first step in one possible algorithm for determining the longitudinal and transverse positions of the first energy deposition event in a scintillator material based on the distributions of the optical photons on the faces of the scintillator. For each of the two scintillators, the positions of the optical photons at the two photodetector panels are determined, as shown for the rear detector of the left camera module in the left-hand panel and for the accompanying front photodetector in the right-hand panel. A time cut is applied to find the photons that arrived earliest, the centroid of these photons is calculated, and a circle is drawn with the centroid as the center and a radius that encompasses a predetermined fixed fraction of the photons on the face, as indicated in the figure. The circles are then used to determine the depth of interaction.

Figure 12B:
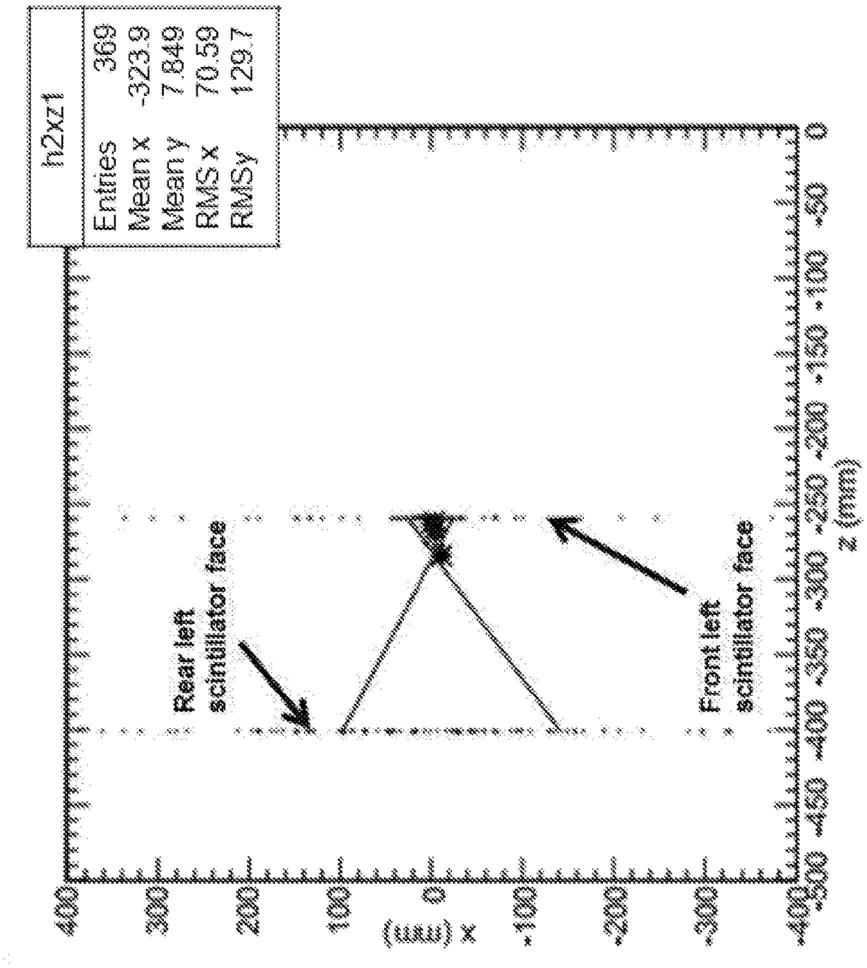
FIG. 12B illustrates how the circles on the photodetector faces are used to determine the longitudinal and transverse positions of the first energy deposition event in a scintillator material.

FIG. 12B illustrates how the circles on the photodetector faces are used to determine the longitudinal and transverse positions of the first energy deposition event in a scintillator material. Cones are drawn between the circles on the front and back faces, and the vertex point is taken as the position of the first gamma interaction in the scintillator.

Figure 13:
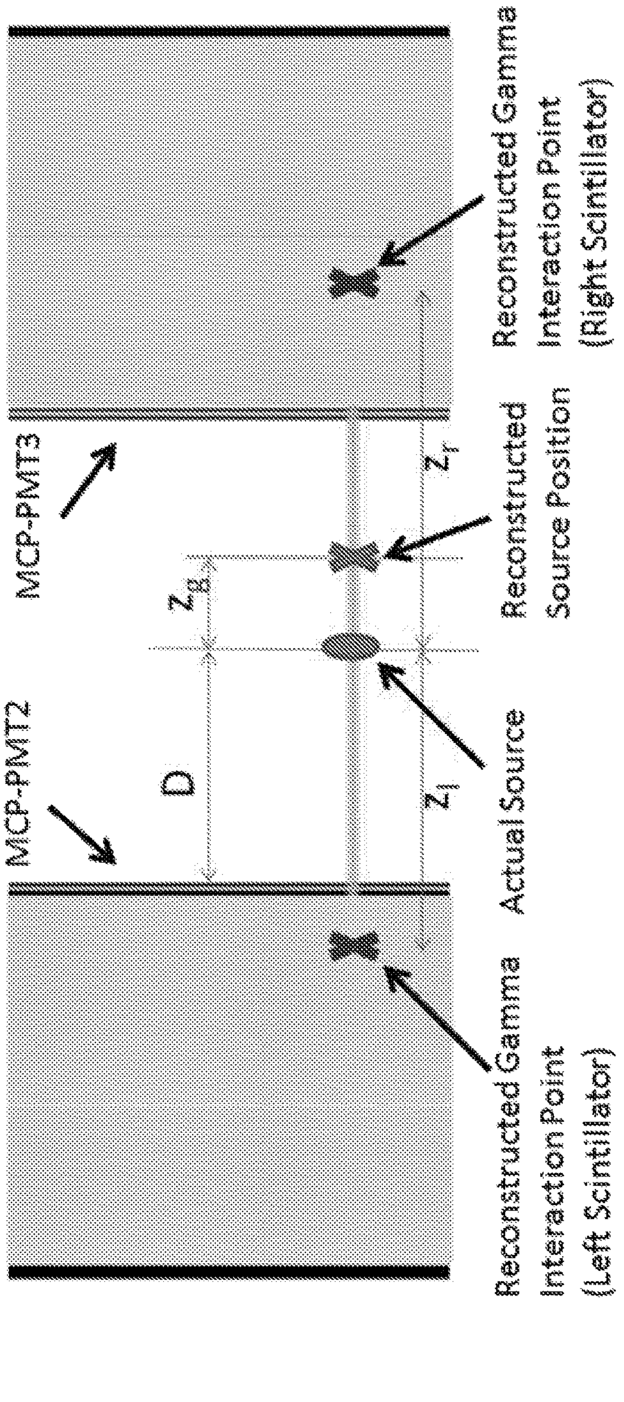
FIG. 13 illustrates one algorithm for calculating the gamma source position based on the positions of the first energy deposition events.

FIG. 13 illustrates one algorithm for calculating the gamma source position based on the positions of the first energy deposition events. A line is drawn between the two interaction points, one in each of the camera modules. The times deduced from the two interaction points are used to determine the position along the line of the positron annihilation which is the source of the two gamma rays.

Figure 14A:
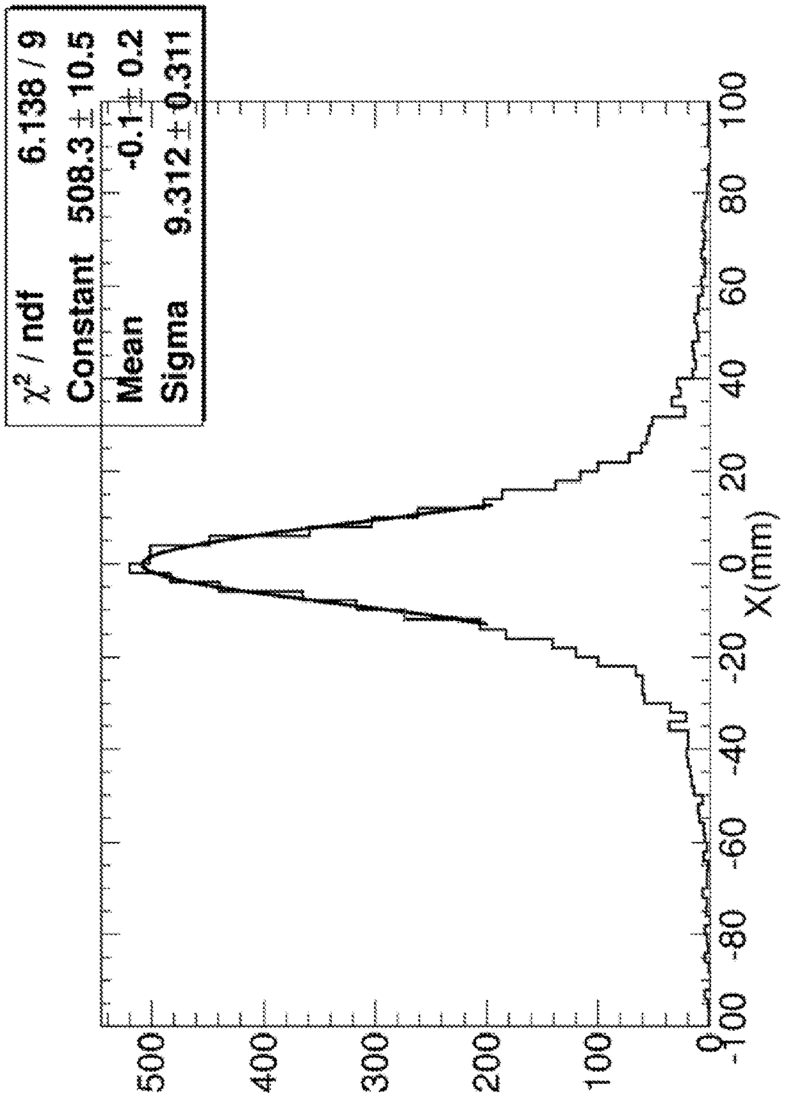
FIG. 14A shows the simulated spatial resolution for the gamma source position in the transverse direction using the nominal light output of the WbLS scintillator.
Figure 14B:
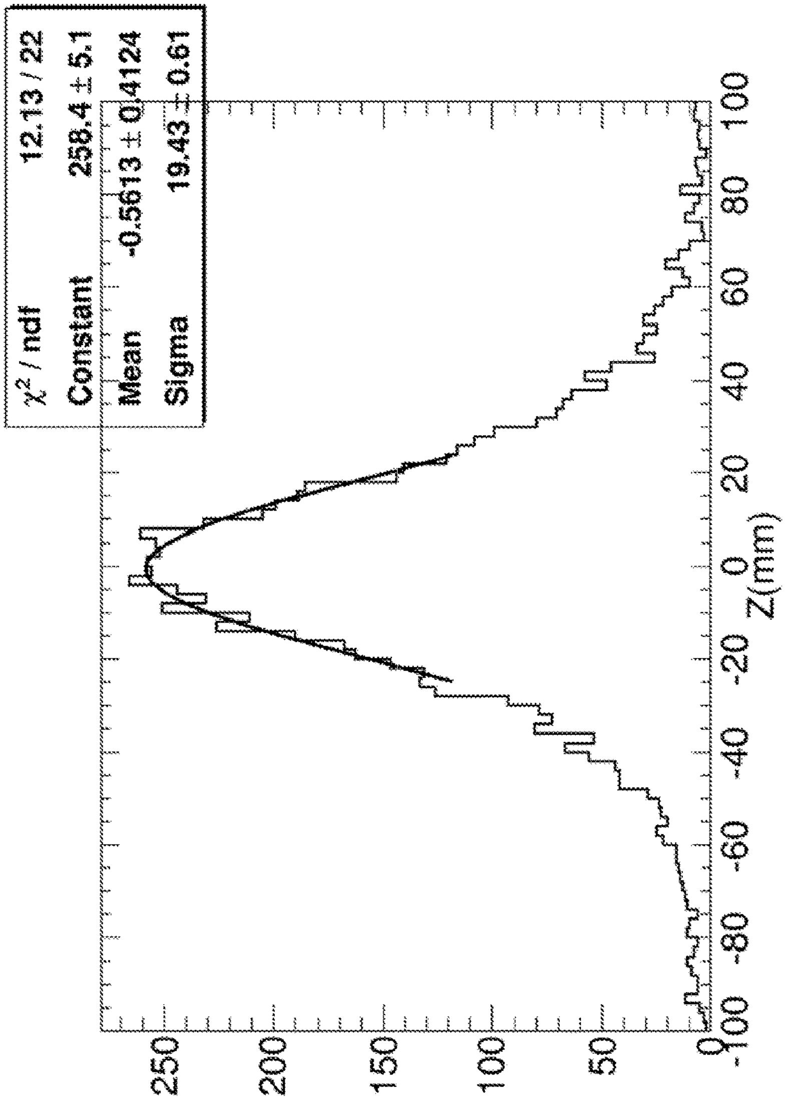
FIG. 14B shows the simulated spatial resolution for the gamma source position in the longitudinal direction using the nominal light output of the WbLS scintillator.
Figure 14C:
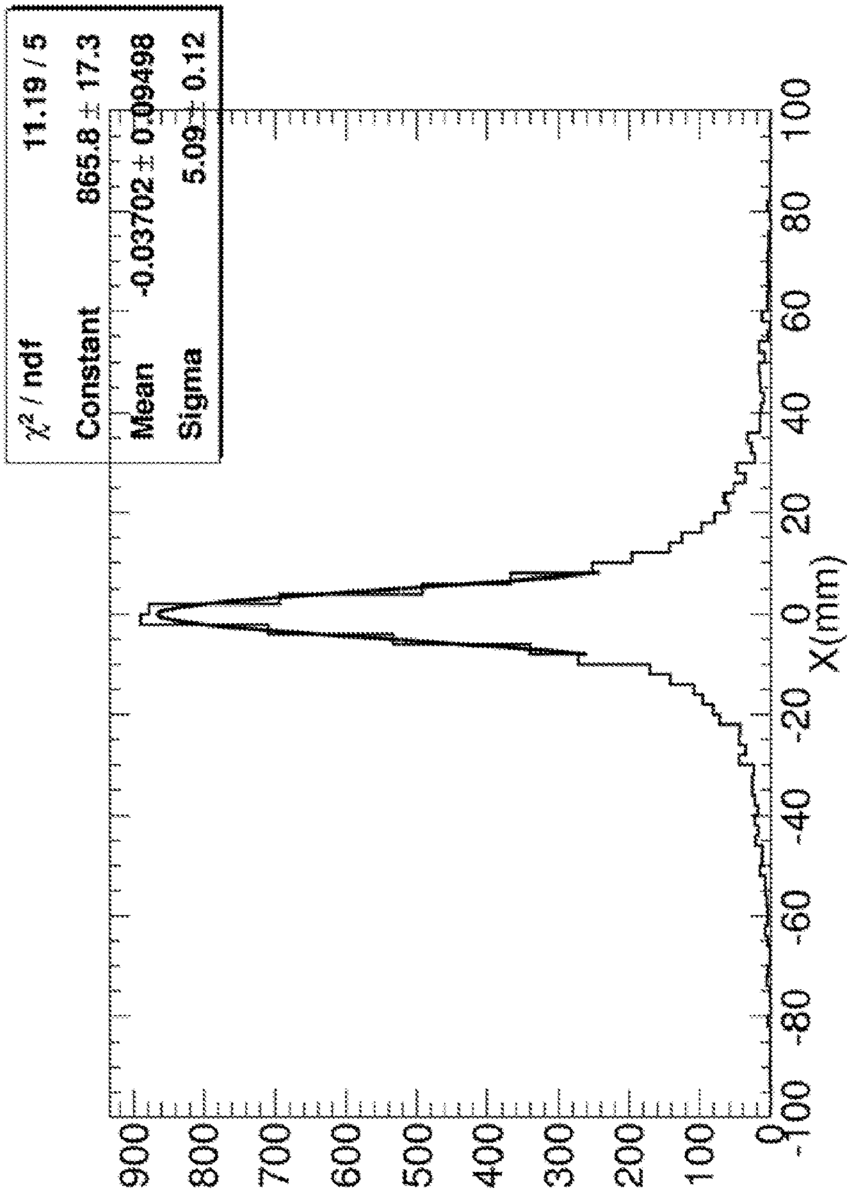
FIG. 14C shows the simulated spatial resolution for the gamma source position in the transverse direction using the nominal light output of a hypothetical WbLS scintillator with 10 times the light output.
Figure 14D:
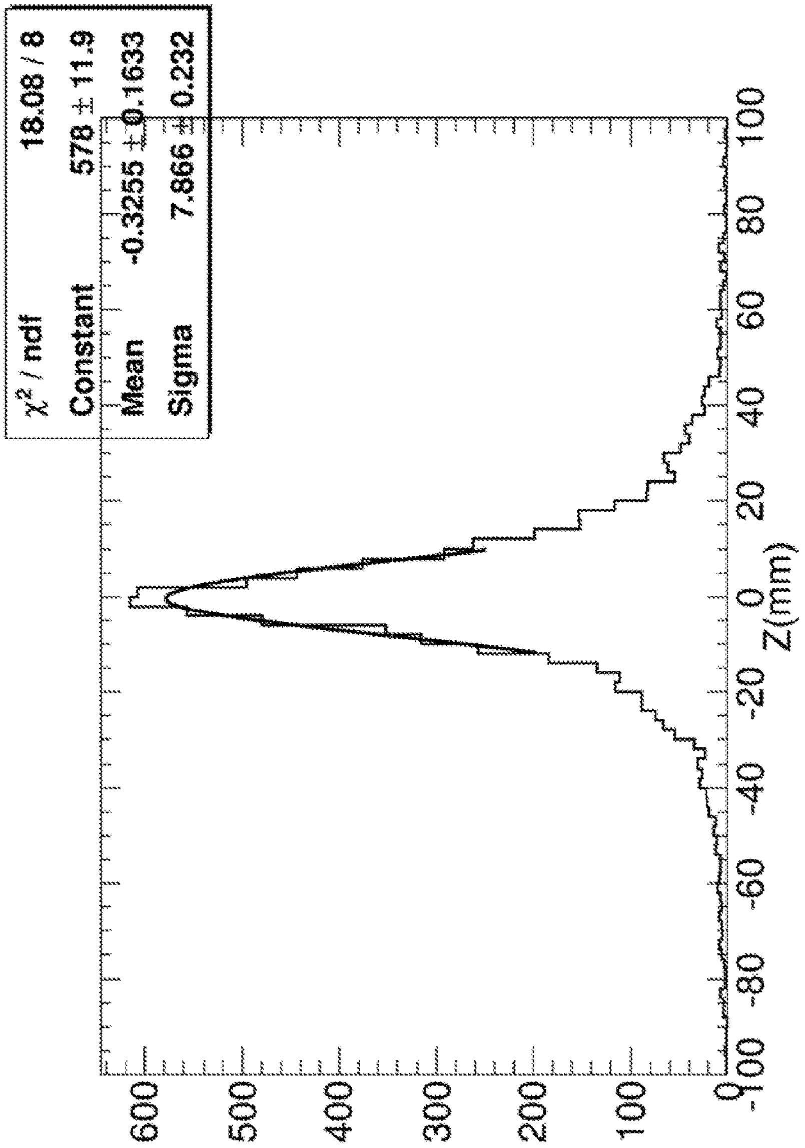
FIG. 14D shows the simulated spatial resolution for the gamma source position in the longitudinal direction using the nominal light output of the hypothetical WbLS scintillator with 10 times the light output.

FIG. 14A shows the simulated spatial resolution for the gamma source position in the transverse direction using the nominal light output of a WbLS scintillator with a scale factor of 1. FIG. 14B shows the simulated spatial resolution for the gamma source position in the longitudinal direction using the nominal light output of the WbLS scintillator. FIG. 14C shows the simulated spatial resolution for the gamma source position in the transverse direction using the nominal light output of a hypothetical WbLS scintillator with 10 times the light output. FIG. 14D shows the simulated spatial resolution for the gamma source position in the longitudinal direction using the nominal light output of the hypothetical WbLS scintillator with 10 times the light output. The resolutions, derived from a fit to the central part of the distribution, are 9.3 mm in the transverse direction and 19.3 mm for the case of the nominal light output, and 5.1 mm and 7.9 mm for the 10-times scaled up light output.

Figure 15:
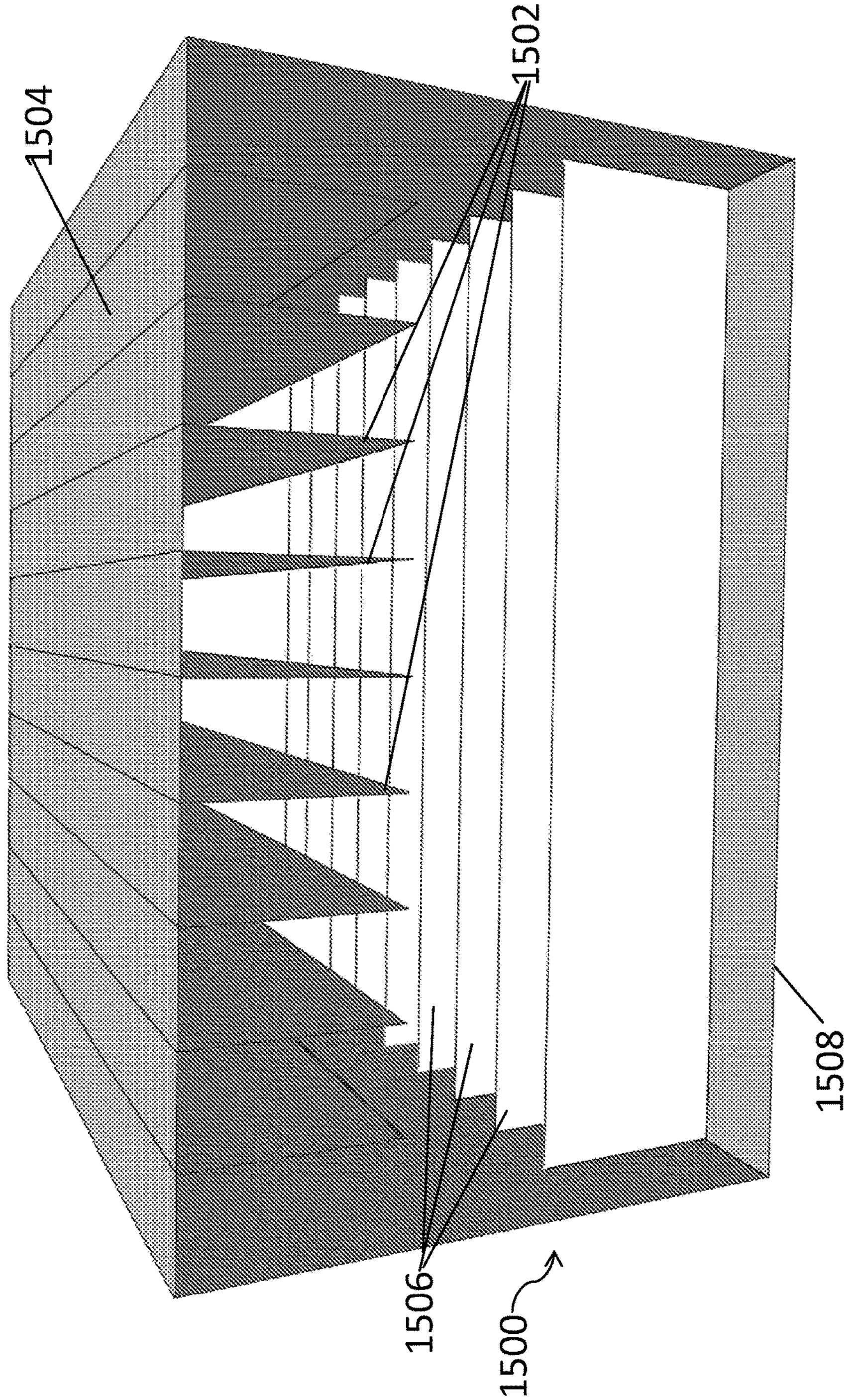
FIG. 15 An example of a camera module configured with internal absorbing and/or reflecting surfaces used to constrain the paths of photons generated in a low-density (for example, liquid) scintillator for a more precise vertex reconstruction.

The present liquid scintillators enable optimization of the light collection paths for improved position and time resolution and/or light collection. The time resolution of the large-area photodetectors is such that differences in arrival time can be used to reconstruct the trajectory of the optical photons, enhancing the collection area and providing additional geometric information on the position of the source. For example, absorbing surfaces, reflecting surfaces, or a combination thereof, can be disposed in or on a face of the first and second liquid scintillator materials and configured to constrain paths of radiation in the first and second liquid scintillator materials. As shown in FIG. 15, the camera module 1500 can be configured with internal light absorbing (e.g., baffles) and/or light reflecting (e.g., mirrors) surfaces 1502 used to constrain the paths of photons generated in the liquid scintillator for a more precise vertex reconstruction. Reflecting surfaces (mirrors) can increase the effective sensitive area of the photodetectors while retaining some point-of-origin information through the drift time of the photons. Absorbing surfaces can limit the angular acceptance of a given area of a photodetector for a more efficient reconstruction. The optimization of the configuration depends on the properties of the scintillator and the photodetectors, and the camera geometry. As illustrated in the embodiment of FIG. 15, reflectors can be positioned in the scintillator volume, as shown, or on the surfaces. The mix of mirrors and baffles can be optimized for different camera geometries; reflectors can be double-sided or single-sided. In FIG. 15, the camera modules includes an upper set of absorbing and/or reflecting surfaces 1502 having a parallel arrangement and extending from the front side 1504 of camera module 1500 into the scintillator volume and a lower set of absorbing and/or reflecting surfaces 1506 having a parallel arrangement and extending from the back side 1508 of camera module 1500 into the scintillator volume. In this embodiment, the reflecting and/or absorbing surfaces of the first set run perpendicular with respect to the absorbing and/or reflecting surfaces of the second set.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A time-of-flight positron-emission tomography detector system comprising:

a sample holder;

a first time-of-flight positron-emission tomography camera module comprising:

a first liquid scintillator material having a front face and a back face;

a first photodetector located on the front face of the first liquid scintillator material, wherein the first photodetector comprises a photocathode, at least one microchannel plate and one or more anodes; and a second photodetector located on the back face of the first liquid scintillator material from the first photodetector, wherein the second photodetector comprises a photocathode, at least one microchannel plate and one or more anodes; and a second time-of-flight positron-emission tomography camera module comprising:

a second liquid scintillator material having a front face and a back face;

a third photodetector located on the front face of the second liquid scintillator material, wherein the third photodetector comprises a photocathode, at least one microchannel plate and one or more anodes; and a fourth photodetector located on the back face of the second liquid scintillator material from the third photodetector, wherein the fourth photodetector comprises a photocathode, at least one microchannel plate and one or more anodes;

wherein the second time-of-flight positron-emission tomography camera module is configured to face the first time-of-flight positron-emission tomography camera module and is located on an opposite side of the sample holder from the first time-of-flight positron-emission tomography camera module.

2. The detector system of claim 1, wherein the first and second liquid scintillator materials are water based scintillator materials.

3. The detector system of claim 2, wherein the water based scintillator materials are loaded with an element having an atomic number greater than 16.

4. The detector system of claim 1, wherein the first and second time-of-flight positron-emission tomography camera modules further comprise absorbing surfaces, reflecting surfaces, or a combination thereof, disposed in or on a face of the first and second liquid scintillator materials and configured to constrain paths of radiation in the first and second liquid scintillator materials.

5. The detector system of claim 1, wherein the first, second, third and fourth photodetectors have time resolutions of 40 psec (sigma) or better for a single photon.

6. The detector system of claim 5, wherein the first, second, third and fourth photodetectors have time resolutions of 30 psec (sigma) or better for a single photon.

7. The detector system of claim 1, wherein the first time-of-flight positron-emission tomography camera module is located above the sample holder and the second time-of-flight positron-emission tomography camera module is located below the sample holder, the detector system further comprising:

a third time-of-flight positron-emission tomography camera module comprising:

a third liquid scintillator material having a front face and a back face;

a fifth photodetector located on the front face of the third liquid scintillator material, wherein the fifth photodetector comprises a photocathode, at least one microchannel plate and one or more anodes; and a sixth photodetector located on the back face of the third liquid scintillator material from the fifth photodetector, wherein the sixth photodetector comprises a photocathode, at least one microchannel plate and one or more anodes; and a fourth time-of-flight positron-emission tomography camera module comprising:

a fourth liquid scintillator material having a front face and a back face;

a seventh photodetector located on the front face of the fourth liquid scintillator material, wherein the seventh photodetector comprises a photocathode, at least one microchannel plate and one or more anodes; and an eighth photodetector located on the back face of the fourth liquid scintillator material from the seventh photodetector, wherein the eighth photodetector comprises a photocathode, at least one microchannel plate and one or more anodes;

wherein the fourth time-of-flight positron-emission tomography camera module is configured to face the third time-of-flight positron-emission tomography camera module and is located on an opposite side of the sample holder from the third time-of-flight positron-emission tomography camera module.

8. The detector system of claim 1, further comprising:

a processor; and a computer-readable medium operably coupled to the processor, the computer-readable medium having computer-readable instructions stored there on that, when executed by the processor:

identifies, on a statistical basis, the position of the first of a plurality of optical photon-emitting Compton Scattering and Photoelectric Effect energy deposition events resulting from an interaction of a first gamma ray of a coincident gamma ray pair with the first liquid scintillator material;

identifies, on a statistical basis, the position of the first of a plurality of optical photon-emitting Compton Scattering and Photoelectric Effect energy deposition events resulting from an interaction of a second gamma ray of the coincident gamma ray pair with the second liquid scintillator material; and calculates the source position for the first and second gamma rays based on the positions of the identified first optical photon-emitting Compton Scattering or Photoelectric Effect energy deposition events in the first and second liquid scintillator materials.

9. The detector of claim 1 further comprising waveform sampling electronic circuitry in communication with the one or more anodes.

10. The detector of claim 1, wherein the one or more anodes comprise transmission line anodes.

11. The detector of claim 1, wherein the one or more anodes are pixel anodes comprising contact pads on a non-vacuum side of the anodes, the detector further comprising readout electronics connected to the pixel anodes.

12. The detector of claim 1 further comprising electronic circuitry connected to the first and second time-of-flight positron-emission tomography camera modules and adapted to detect a pair of coincident gamma rays emanating from a sample.

13. A method of imaging a gamma ray-emitting region in a sample, the method comprising:

placing a sample that emits coincident gamma ray pairs between a first time-of-flight positron-emission tomography camera module comprising a first scintillator material and a second time-of-flight positron-emission tomography camera module comprising a second scintillator material;

detecting coincident gamma ray pairs in which the first gamma ray interacts with a volume of the first scintillator material to produce a plurality of optical photon-emitting Compton Scattering and photoelectric energy deposition events in the same volume of the first scintillator material with which the first gamma ray interacted and the second gamma ray interacts with a volume of the second scintillator material to produce a plurality of optical photon-emitting Compton Scattering and photoelectric energy deposition events in the same volume of the second scintillator material with which the second gamma ray interacted;

determining source positions for the detected coincident gamma ray pairs by:

identifying, on a statistical basis, the first of the plurality of optical photon-emitting Compton Scattering and photoelectric energy deposition events produced in the first scintillator material by the first gamma ray of a coincident gamma ray pair;

identifying, on a statistical basis, the first of the plurality of optical photon-emitting Compton Scattering and photoelectric energy deposition events produced in the second scintillator material by the second gamma ray of the coincident gamma ray pair; and calculating a source position for the coincident gamma ray pair based on the positions of the identified first optical photon-emitting Compton Scattering or photoelectric energy deposition events in the first and second scintillator materials; and generating an image of a gamma ray-emitting region in the sample based on the calculated source positions.

14. The method of claim 13, wherein the calculated source positions have uncertainties of no greater than 2 mm in any direction, based on the time resolutions of the first and second time-of-flight positron-emission tomography camera modules.

15. The method of claim 13, wherein the first and second scintillator materials are liquid scintillator materials.

16. The method of claim 13, wherein the first and second scintillator materials are water based scintillator materials.

17. The method of claim 16, wherein the water based scintillator materials are loaded with an element having an atomic number greater than 16.

18. The method of claim 13, wherein the sample is a human patient.

19. The method of claim 13, wherein the identified first optical photon-emitting energy deposition events in the first and second scintillator materials are Compton Scattering events.

20. The method of claim 13, wherein the first and second gamma rays of the coincident gamma ray pairs have a coincidence window of no greater than about 50 psec.

21. The method of claim 13, wherein the coincident gamma ray pairs upon which the image is based include coincident gamma ray pairs in which the first gamma ray has a deposition energy inside of a 511 KeV energy peak and the second gamma ray has a deposition energy outside of a 511 KeV energy peak.

22. The method of claim 21, further comprising:

assigning weighted values to the source positions for the coincident gamma ray pairs based on the deposition energies of their first and second gamma rays, such that source positions for coincident gamma ray pairs in which both gamma rays have deposition energies inside the 511 KeV energy peak have a higher weighted value than the source positions for coincident gamma ray pairs in which one of the gamma rays has a deposition energy outside the 511 KeV energy peak; and depicting source positions having higher weighted values with higher intensities in the image.

23. The method of claim 22, further comprising:

revising the weighted values of the source positions based on their proximity to other source positions, such that source positions close to other source positions have a higher revised weighted value than source positions that are not close to other source positions; and revising the image, as the sample continues to emit coincident gamma ray pairs, to reflect the revised weighted values.

24. The method of claim 13, wherein the source of the emitted gamma ray pairs in the sample is a positron-emitting radioisotope.

25. The method of claim 13, wherein the source of the emitted gamma rays is the annihilations of positrons from a beam of hadrons directed into the sample.

26. A method of imaging a gamma ray-emitting region in a sample, the method comprising:

placing a sample that emits coincident gamma ray pairs between a first time-of-flight positron-emission tomography camera module comprising a first scintillator material and a second time-of-flight positron-emission tomography camera module comprising a second scintillator material; detecting coincident gamma ray pairs in which the first gamma ray interacts with the first scintillator material to produce a first sequence of optical photon-emitting Compton Scattering events in the first scintillator material and the second gamma ray interacts with the second scintillator material to produce a second sequence of optical photon-emitting Compton Scattering events in the second scintillator material; resolving, on a statistical basis, the locations in the first scintillator material of an earlier optical photon-emitting Compton Scattering event and a later optical photon-emitting Compton Scattering event in the first sequence; resolving, on a statistical basis, the locations in the second scintillator material of an earlier optical photon-emitting Compton Scattering event and a later optical photon-emitting Compton Scattering event in the second sequence; calculating a source position for the coincident gamma ray pair based on the locations of the optical photon-emitting Compton Scattering events in the first and second scintillator materials; and generating an image of a gamma ray-emitting region in the sample based on the calculated source positions.

27. The method of claim 26 further comprising: determining the initial direction of the first gamma ray based on the locations of the earlier and later optical photon-emitting Compton Scattering events in the first sequence; and determining the initial direction of the second gamma ray based on the locations of the earlier and later optical photon-emitting Compton Scattering events in the second sequence.

* * * * *